(12) United States Patent
Friesner et al.

(10) Patent No.: US 8,145,430 B2
(45) Date of Patent: Mar. 27, 2012

(54) PREDICTIVE SCORING FUNCTION FOR ESTIMATING BINDING AFFINITY

(75) Inventors: Richard A. Friesner, New York, NY (US); Robert Murphy, Englewood Cliffs, NJ (US)

(73) Assignee: Schrodinger, LLC, New York, NY (US)

( * ) Notice: Subject to any disclaimer, the term of this patent is extended or adjusted under 35 U.S.C. 154(b) by 1082 days.

(21) Appl. No.: 11/373,684

(22) Filed: Mar. 10, 2006

(65) Prior Publication Data

US 2007/0061118 A1    Mar. 15, 2007

Related U.S. Application Data

(60) Provisional application No. 60/660,822, filed on Mar. 11, 2005.

(51) Int. Cl.
*G06G 7/48*    (2006.01)
*G06G 7/58*    (2006.01)

(52) U.S. Cl. .................. 702/19; 702/27; 703/11

(58) Field of Classification Search .............. None
See application file for complete search history.

(56) References Cited

U.S. PATENT DOCUMENTS

| | | | |
|---|---|---|---|
| 6,671,628 | B2 | 12/2003 | Hurst |
| 6,741,937 | B2 | 5/2004 | Waldman et al. |
| 2003/0215877 | A1 | 11/2003 | Love et al. |
| 2004/0267510 | A1 | 12/2004 | Bemis et al. |
| 2005/0027458 | A1 | 2/2005 | Merz et al. |

FOREIGN PATENT DOCUMENTS

| | | |
|---|---|---|
| JP | 2003-263465 | 9/2003 |
| JP | 2005-242493 | 9/2005 |
| JP | 2005-293296 | 10/2005 |
| WO | 96/13785 | 5/1996 |
| WO | WO 2005/008240 | 1/2005 |

OTHER PUBLICATIONS

Stahl et al. Detailed Analysis of Scoring Functions for Virtual Screening. Med. Chem., 2001, 44 (7), pp. 1035-1042.*

Freisner et al. J.. Med. Chem., 2004, 47 (7), pp. 1739-1749.*
Clausen et al., "The FlexX Database Docking Environment—Rational Extraction of Receptor Based Pharmacophores" Current Drug Discovery Technologies, vol. 1, pp. 49-60, (2004).
Friesner et al., "Glide: A New Approach for Rapid, Accurate Docking and Scoring. 1. Method and Assessment of Docking Accuracy," J. Med. Chem. 2004, 47, 1739-1749.
Gohlke et al., "Knowledge-based Scoring Function to Predict Protein-Ligand Interactions", J. Mol. Biol., vol. 295, pp. 337-356, (2000).
Halgren et al., "Glide: A New Approach for Rapid, Accurate Docking and Scoring. 2. Enrichment Factors in Database Screening," J. Med. Chem. 2004, 47, 1750-1759.
McConkey et al., "The performance of current methods in ligand-protein docking", Current Science, vol. 83, No. 7, pp. 845-856, (2002).
Schwarz et al., Rigid Receptor-Flexible Ligand Docking: Overview and Examples, Version 1.2: Aug. 13, 2003 18:47:44.457 GMT-5, Connexions module: m11464; http://creativecommons.org/licenses/by/1.0.
Wang et al., "Score: A New Empirical Method for Estimating the Binding AffinityAffinityof a Protein-Ligand Complex", J. Mol. Model., vol. 4, pp. 379-394, (1998).

* cited by examiner

*Primary Examiner* — Michael Borin
(74) *Attorney, Agent, or Firm* — Fish & Richardson P.C.

(57) ABSTRACT

A computer-implemented method for calculating a value representative of interaction (VRI) of a proposed ligand with a specified receptor. Hydrophobic interactions between one or more ligand atoms and one or more receptor atoms are scored by a method that awards a bonus for the presence of hydrophobic enclosure of one or more ligand atoms by the receptor. Also, charge-charge hydrogen bonds between a ligand and a receptor are scored by setting a default value for a charge-charge hydrogen bond and awarding a bonus above the default value when one or more specialized predetermined charge-charge hydrogen bond criteria is satisfied. Various charge-charge hydrogen bond criteria are used. Zwitterions, charge, salvation, geometry and electrostatic energy are accounted for.

40 Claims, 11 Drawing Sheets

(8 of 11 Drawing Sheet(s) Filed in Color)

PREDICTIVE SCORING FUNCTION FOR ESTIMATING BINDING AFFINITY

RELATED APPLICATION INFORMATION

This application claims priority to U.S. provisional application Ser. No. 60/660,822, filed Mar. 11, 2005, which is hereby incorporated by reference.

BACKGROUND OF THE INVENTION

The invention relates to a predictive scoring function for estimating binding affinity.

A great majority of pharmaceutically active compounds derive efficacy from binding to targeted receptors which are often proteins (a term that includes glycoproteins and lipoproteins). Approximately 50 years ago, the first high resolution structure of a protein was determined via x-ray crystallography. The publicly accessible protein data bank (PDB) now contains more than 10,000 such structures, and pharmaceutical and biotechnology companies have an order of magnitude more proprietary structures. Many of these structures have been co-crystallized with small molecules bound to them. The examination of such structures, and deployment of the knowledge thereby gained to design new, more potent, and more specific inhibitors, is referred to as structure-based drug design.

Computational modeling facilitates structure-based drug design. Given a high resolution protein structure, computational software is used to "dock" a small molecule ligand into the correct position and orient it in the protein active site cavity, and calculate a binding affinity of the ligand given this structure. Computer software programs that perform this task are referred to as "docking" programs.

A docking program typically carries out two distinct tasks to model protein-ligand binding. First, a structure of a protein-ligand complex is predicted. In high throughput docking, a receptor (e.g., protein) is ordinarily assumed to be rigid. When this assumption fails, use of a different structure of the receptor as a starting point is required. The problem of constructing alternative receptor structures that are modified to accept ligands requiring a substantial change in receptor conformation ("induced fit") is a very important one. We focus here on cases where docking of the ligand into a rigid receptor yields a structure in reasonable agreement with experimental data. This will be the case when, in the docked structure, the ligand in the docked structure makes key hydrogen bonds and hydrophobic contacts with the protein in good agreement with the experimental data.

A second task of the docking program is to calculate a protein-ligand binding affinity, given as an input the docked structure. A mathematical function employed to calculate the binding affinity is referred to as a "scoring function." Despite intensive effort over several decades, in many situations, presently available scoring functions are unsatisfactory with regard to the desired accuracy and robustness.

SUMMARY OF THE INVENTION

There are two aspects of the invention, both of which feature a computer-implemented method for calculating a value representative of interaction (VRI) of a proposed ligand with a specified receptor.

Generally stated, in the first aspect, hydrophobic interactions between one or more ligand atoms and one or more receptor atoms are scored by a method that awards a bonus for the presence of hydrophobic enclosure of one or more ligand atoms by the receptor, and the bonus results in a VRI indicative of enhanced ligand/receptor binding affinity.

In preferred embodiments of the first aspect of the invention, calculation of VRI includes at least one term representative of free energy, enthalpy or entropy, or a combination thereof. Scoring hydrophobic interactions may include calculating a surface area scoring component (SASC) that varies as a function of the surface area of hydrophobic-hydrophobic contact between ligand atoms and receptor atoms, and the bonus for the presence of hydrophobic enclosure results in an increase in VRI relative to a hypothetical VRI that would be obtained using the SASC but not the bonus. Scoring can also include calculating an atom-atom pair energy term, so that the bonus for the presence of hydrophobic enclosure results in an increase in VRI relative to a hypothetical VRI that would be obtained using the sum of atom-atom pair energy term but not the bonus. Scoring hydrophobic interactions may further include calculating an atom-atom pair energy term, and the bonus for the presence of hydrophobic enclosure results in an increase in VRI relative to a hypothetical VRI that would be obtained using the sum of atom-atom pair energy terms plus the SASC term, but not the bonus.

The calculated VRI value may be used in various ways, for example, by a computer program in a method to simulate docking of the ligand into the receptor to produce the structure of the receptor-ligand complex, e.g., to assist in assigning a structure to the receptor-ligand complex or to assess binding affinity of the ligand to a protein-ligand complex structure produced by the docking program.

Alternatively, the VRI value may be calculated in a method that assigns a value representative of receptor-ligand interaction in a pre-determined receptor-ligand structure, for example, a pre-determined receptor-ligand structure obtained from a docking program, from molecular dynamics simulations or from minimizations using a continuum solvation model.

Preferably, a graphical display of structural features of the receptor-ligand complex that contribute to enhanced VRI due to hydrophobic enclosure is generated when the scoring indicates the presence of hydrophobic enclosure, and receptor atoms contributing to the hydrophobic enclosure of one or more ligand atoms may be graphically highlighted provide a physical picture of the enclosure. Surfaces of the receptor that are involved in hydrophobic enclosure of the ligand may also be highlighted in the display.

The first aspect of the invention may be used to select compounds to be tested experimentally.

Preferred embodiments of the first aspect of the invention may include one or more of the following steps in any order (except that step g) is performed last): a) calculating a term representing hydrophobic enclosure; b) calculating a term representing electrostatic rewards; c) calculating a term enhancing VRI for hydrogen (H) bonds in hydrophobic regions; d) calculating a term representing H bond pairs; e) calculating terms representing $\pi$-cation and $\pi$ stacking; f) calculating a term representing a standard lipophilic pair; and g) calculating the score from a sum of terms. The presence of hydrophobic enclosure may be determined by performing at least the following steps: a) locating lipophilic receptor atoms that are within a specified cut-off distance of a hydrophobic atom of the ligand; b) determining the spatial and angular distribution of lipophilic receptor atoms around the hydrophobic ligand atom; c) awarding the bonus based on the spatial and angular distribution of the lipophilic receptor atoms around the hydrophobic ligand atom. The presence and magnitude of hydrophobic enclosure may be determined by performing at least the following steps: a) dividing lipophilic atoms of the ligand into groups of atoms that are connected by co-valent bonds; and b) assigning a hydrophobic enclosure score to each group, and setting the enclosure score to zero if the size of the group is below a prespecified threshold value (for example, by determining a hydrophobic enclosure score for each ligand atom in the group, and then adding the values for each ligand atom to obtain the group score); c) calculating the total bonus to be awarded for hydrophobic enclosure as a sum of hydrophobic enclosure scores of the connected groups. The value of the hydrophobic enclosure score for a ligand atom in a suitable connected group may be determined by performing at least the following steps: a) calculate the distance between the ligand atom and the lipophilic atoms of the receptor; b) employ a mathematical formula to assess the degree of enclosure of the atom where the formula takes into account the angular dispersion of the lipophilic receptor atoms and their distance from the ligand atom. Greater angular dispersion of receptor atoms that are within the specified cut-off distance of the ligand atom will result in a higher enclosure score using said formula, and a ligand atom which is enclosed by lipophilic receptor atoms at suitably short distances will yield a nonzero enclosure score using said formula. Also, the hydrophobic enclosure score of each ligand atom in the group is determined by a method that includes the following steps: a) designate an anchor atom which is the lipophilic receptor atom that is closest to the ligand atom; b) construct a reference vector between the ligand atom and the anchor atom; c) construct vectors between the ligand atom and remaining lipophilic receptor atoms within a specified distance cutoff; d) calculate the angle formed between each of the vectors defined in c) and the reference vector; and e) determine the contribution of the lipophilic receptor atom generating the vector in c) to the enclosure score by the distance of the receptor atom to the ligand atom, and by the angle defined in d), using a function in which contribution increases with decreasing distance and with increasing angle. The contribution to enclosure for each lipophilic receptor atom is a product of the angular score and the distance score. The angular score is set as zero if the angle is less than a predetermined angle, which may but need not vary as a function of increasing distance between the ligand atom and the anchor atom. Ligand atoms may be assigned to a lipophilic group that includes a set of connected carbon atoms uninterrupted by polar atom connections, omitting carbon atoms connected to polar atoms. The groups may contain a minimum number of atoms (e.g., at least three atoms). A condition may be set that lipophilic receptor atoms receiving a nonzero enclosure score must be within a distance that is the sum of a constant (e.g. approximately 3 Å±0.1 Å) plus the sum of the van der Waals radii of the ligand and the receptor. The division of atoms into connected groups of ligand atoms may involve a mathematical operation that is a function of bonding connectivity and of chemical identity of each atom and its neighbors.

In one preferred embodiment, the ligand includes groups of neutral atoms and the method includes: identifying one or more hydrogen bonds between the neutral ligand atoms and the receptor by employing distance and angular criteria; determining atoms of the ligand connected to the hydrogen bonding group or groups; assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure. A single hydrogen bond of the ligand with the receptor is detected, and a special single hydrogen bond bonus is awarded if that hydrogen bond and its environment satisfy one or more (most preferably all) of the following conditions: (a) a hydrogen bond donor or acceptor atom of the ligand is: i) nitrogen; ii) in a ring or iii) both (i) and (ii); (b) a ligand atom forms part of a group of hydrogen bond donor atoms and all donors of the group are hydrogen bonded to the receptor; (c) the receptor is a protein and receptor atoms participating in the hydrogen bond are part of the protein backbone; (d) the relevant receptor donor or acceptor atom in the apoprotein structure (i.e., the structure of the receptor with no ligand present) is poorly solvated (e.g., using a grid based water addition program to assess the solvation of the donor or acceptor atom in an apoprotein structure of the receptor; (e) the sum of the angular factors in the enclosure terms for the ligand heavy atom involved in the hydrogen bond and any carbon atoms attached to this atom is calculated, and the sum is required to exceed a specified threshold (e.g., by making a small perturbation of the ligand and assessing whether the perturbation improves the enclosure score so as to exceed the threshold). For example, a special single hydrogen bond bonus of about −1.5±0.3 kcal/mole may be assigned when all of the criteria (a)-(e) above are satisfied. Criteria (e) may be imposed as described above or by itself. Atoms may be required to have fewer than three waters in contact in order to qualify for the special hydrogen bond bonus. Other possible criteria for awarding a special pair hydrogen bond bonus include one or more of the following: (a) pairs of multiple hydrogen bonds do not qualify for the special pair hydrogen bond bonus when the bonding atoms are separated by more than one rotatable bond, where OH groups count as non-rotatable in this calculation; and/or (b) one or more of the following types of pairs of ligand receptor hydrogen bonds do not qualify for the special pair hydrogen bond bonus:

1) poor quality H bonds (<0.05 HB pair score);
2) pairs involving the same neutral protein atom;
3) pairs involved in a salt bridge if the electrostatic potential at either ligand atom is not below a cutoff;
4) salt bridge pairs if either receptor atom is involved in a protein—protein salt bridge;
5) ligand donor/donor pairs which come from NH_x x >= 2 groups where N is not part of a ring and has zero formal charge;
6) formally charged protein atoms with more than 8 second shell waters in the unligated state;
7) charged-neutral H bonds where the protein atom is not in a salt bridge;
8) pairs of different neutral acceptor atoms on the ligand;
9) Neutral H bond pairs that do not qualify individually for a single hydrogen bond reward, e.g., they do not satisfy ring atom and phobicity environment checks; and
10) ligand OH to receptor H bonds if the receptor atom has zero formal charge.

(c) for pairs in which the ligand atoms of the pair individually have zero net formal charge, the hydrogen bonds are awarded a bonus for said hydrophobic enclosure where scoring said hydrophobic interaction is optimized for hydrogen bond pairs. The following conditions are used in performing step (c) above to determine whether the hydrogen bond pair has a hydrophobic enclosure score above a cut-off score so as to receive the hydrogen bond pair bonus: a) ligand atoms in the pair must be part of the same ring or, for non-ring ligand atoms, the ligand atoms must be directly connected to the same ring; and b) hydrophobicity of a hydrogen bond region is detected and angular factors for enclosure terms are added and the sum exceeds a specified cut-off using the pair of hydrogen bonding ligand atoms and the ligand ring atoms directly connected to the ligand atoms participating in the hydrogen bond; and c) if a ligand atom of the pair is not a ring atom but is connected to a ring, the above sum includes atoms of the ring which are next neighbors to the non-ring ligand atom. Double counting of pair and single special hydrogen bonds may be avoided by looking for pairs first and excluding any rewarded hydrogen bonds found in the pair list from the single H bond reward list. Additional criteria are: d) ligand atoms in the pair must be part of the same ring or, for non-ring ligand atoms, the ligand atoms must be directly connected to the same ring; and e) hydrophobicity of a hydrogen bond region is detected and the sum of the angular factors in the enclosure terms for the ligand heavy atom involved in the hydrogen bond and the ligand ring atoms directly connected to the ligand atoms participating in the hydrogen bond, where the sum is required to exceed a specified threshold; f) if a ligand atom of the pair is not a ring atom but is connected to a ring, the sum includes atoms of the ring which are next neighbors to the non-ring ligand atom; and g) the bonus awarded to the hydrogen bond pair is about −3 kcal/mole.

Steps for evaluating the magnitude of the bonus for hydrophobic enclosure are: determining the presence of singlet hydrogen bonds, correlated pairs of hydrogen bonds and triplets of hydrogen bonds, and assigning different per-bond values to singlet, pair, and triplets of hydrogen bonds. A value for hydrogen bonds between groups of neutral atoms of a ligand and a receptor may be assigned by a method comprising, assessing the degree of solvation of the receptor, and awarding a neutral-neutral hydrogen bond reward depending on the degree of receptor solvation. Two pairs of hydrogen bonds sharing an atom in common may satisfy the criteria for awarding a bonus, and the bonus for the second pair may be specifically set, for example, at about −2 kcal/mole. The bonus assigned to the pair of hydrogen bonds (referred to below as the "base reward") may be reduced according to the following formulation:

scaling the base reward down using an angular function:

$$S(\theta)=(\theta-\theta_m)/(\theta_0-\theta_m), \text{ if } \theta_m<\theta<\theta_0$$

where $\theta_0$ is the maximal angle and $\theta_m$ is the minimal angle allowed in the parametrization, $S(\theta)=1.0$, if $\theta \geq \theta_0$ and $S(\theta)=0.0$, if $\theta<\theta_m$ assigning each bond of the pair an angular scale factor $S1$, $S2$; and applying the product ($E_{hb\_spec}$) of the angular scale factor for each bond $S1*S2$ of the pair to the base reward ($E_{base}$), according to the formula $E_{hb\_spec}=S1*S2*E_{base}$.

For example, $\theta_0$ may be set at $135°\pm5°$ and $\theta_m$ may be set at $120°\pm5°$. Solvation of hydrogen bonding partners of the protein in a neutral-neutral hydrogen bond may be evaluated by applying a grid-based algorithm for adding explicit waters, and counting the number of such waters in the first and second shell around the protein group in question.

A computer-generated depiction of the complex may be generated in which hydrogen bonds receiving a special bonus due to hydrophobic enclosure are highlighted in a graphical display. Enclosure of hydrogen bonds receiving a special bonus due to hydrophobic enclosure may also be highlighted in the computer-generated graphical display, for example, receptor atoms participating in the hydrophobic enclosure of hydrogen bonds receiving a bonus are highlighted in a graphical display. Receptor atoms participating in the hydrophobic enclosure of hydrogen bonds receiving a bonus also may be highlighted via a display of hydrophobic surfaces of the receptor. Ligand atoms connected to hydrogen bonds receiving a special bonus due to hydrophobic enclosure may also be highlighted in a graphical display.

Regions of the receptor capable of providing hydrophobic enclosure to suitable ligand groups may be detected by carrying out molecular dynamics simulations, and identifying regions where the water molecules have unfavorable chemical potentials.

Regions of the receptor capable of providing hydrophobic enclosure to suitable ligand groups may be detected by placing water molecules surrounding the receptor and detecting enclosed environments of these water molecules.

In the second aspect of the invention, charge-charge hydrogen bonds between a ligand and a receptor are scored by: setting a default value for a charge-charge hydrogen bond, and awarding a bonus above the default value when one or more specialized predetermined charge-charge hydrogen bond criteria is satisfied. The charge-charge hydrogen bond criteria include one or more of the following: determining whether a ligand has a net charge or is a zwitterion in determining whether to award the bonus, in determining the value of the bonus, or both, determining the distance between oppositely charged groups if the ligand is a zwitterion, determining the degree of solvation of the receptor group involved in the hydrogen bond, determining the detailed geometry of the charge-charge hydrogen bond, and determining the electrostatic energy of the charge-charge hydrogen bond. For example, a zwitterion may be assigned an additional charge-charge bonus if both the positive and negative groups in the zwitterion form charge-charge hydrogen bonds, and if the distance between the groups does not exceed a predetermined distance. The bonus may increase as the electrostatic interaction of the charge-charge hydrogen bonds formed by the zwitterion with the receptor increases. The bonus also may increase (e.g., from 3.0±0.5 kcal/mole to 4.7±0.5 kcal/mole) as the size of the electrostatic interactions increases.

Receptor solvation may be assessed and a charge-charge hydrogen bond reward assigned if receptor solvation is below a predetermined value, e.g., approximately 9 second shell waters, as determined by a grid-based water addition code, around the charged receptor atom involved in the charge-charge hydrogen bond. Also, an additional charge-charge hydrogen bond reward may be assigned if the electrostatic energy of receptor and ligand exceed a specified threshold.

Preferably, the second aspect of the invention includes determining whether interaction of positively and negatively charged groups in the charge-charge hydrogen bond is bidentate or monodentate, and assigning an additional charge-charge hydrogen bond reward for bidentate bonds. Thus, a determination is made whether multiple charged groups of the receptor are involved in the structure, and a special bonus is assigned if multiple charged groups are involved in the structure. If the ligand group is a carboxylate group the bonus assigned for interaction with multiple positively charged receptor groups may be 1.0±0.3 kcal/mole.

The zwitterion's charge-charge reward is determined by: determining the number of waters surrounding the receptor component of the charged atoms bridging the receptor and the ligand and eliminating or reducing charge-charge rewards where the charges are fully hydrated; and classifying hydrogen bonds as: a) monodentate; b) bidentate within a ligand group; or c) bidentate bridging from one ligand group to two different protein groups and adjusting the charge-charge reward based on that classification, to recognize that monodentate hydrogen bonds have a lower value than internal bidentate hydrogen bonds, which in turn have a lower value than bridging bidentate hydrogen bonds.

Preferably, the method includes using a grid based water addition code to assess solvation of the receptor partner of the charge-charge hydrogen bond in the absence of ligand.

Also preferably, a charged atom in an electrostatic environment having a value that exceeds a specified cut-off is given a special bonus, e.g., 1.5 kcal/mole±0.3 kcal/mole.

In other preferred embodiments, a component of VRI represents charge-charge hydrogen bonds or interactions and that component is added to other scoring components to calculate the total free energy of the ligand bound to the receptor.

Finally, charge-charge hydrogen bonds receiving the special bonus may be highlighted in the graphical display.

In evaluating hydrogen bonds in the second aspect of the invention, it may be important to evaluate charges on ligand atoms. For any given ligand, "partial charges" may be assigned to each atom based on the force field that is being used for the molecular modeling calculation. One suitable force field is Optimized Potential for Liquid State (OPLS) OPLS and other force fields generally have well defined algorithms for assigning partial charges to atoms.

The partial charges can be alternatively expressed as "bond charge increments" and "net charges". Bond charge increments are equal and opposite charges spread across a specific bond. Bond charge increments, being composed of equal and opposite charges, are by definition neutral. Once the bond charge increments are defined (in OPLS, these increments are in fact used to construct the partial charges), they can be summed to give partial charges on each atom which are the charges that would be obtained if there were no net charges. The net charges are then the difference between the charge obtained by summing the bond charge increments, and the actual partial charges.

A neutral-neutral hydrogen bond is one in which none of the partner atoms have any net charges as defined above. A charge-charge hydrogen bond is one in which the atoms of the ligand and receptor involved in the hydrogen bond both have net charges (of opposite sign).

The invention can be implemented to realize one or more of the following advantages.

Improved terms of a scoring function are provided by assuming binding in a protein-ligand complex is predominantly driven by finding water molecules that are badly positioned in the protein and replacing them with a ligand in a suitable fashion.

Methods described herein enable one to semi-quantitatively rank the ability of candidate ligands to bind to a specified conformation of the protein receptor. The root mean square (RMS) error in computing the binding affinities of ~120 PDB complexes of the scoring function using the new terms is 1.8 kcal/mole, as opposed to 3.3 kcal/mole for an alternative scoring function whose performance is typical of those in the literature. This improvement of nearly a factor of two in absolute binding affinity prediction translates into a qualitatively better ability to rank order compounds.

Methods described herein enable one to carry out virtual screening calculations on large compound libraries (thousands to millions of compounds) and substantially enrich the fraction of active compounds in the top scoring component of the library, thus enabling these compounds to be selected for experimental evaluation, and avoiding experimental evaluation of lower ranked compounds which are much less likely to be active. The enrichment factors obtained with the new scoring function are often ~10 times larger than those obtained without the methods described herein.

Methods described herein enable one to carry out lead optimization of an active compound, by predicting the binding affinity to be lost or gained by replacing one functional group of the compound with a chemically accessible alternative. The improved accuracy in binding affinity prediction obtained is critical to lead optimization efforts. If the errors are too large, the probability of obtaining an improved molecule based on a scoring function becomes insufficiently large to justify its use in a practical context.

Methods described herein enable an assessment of the selectivity of binding of a molecule against two different protein targets. The molecule can be docked into both targets, and the scores can be compared to estimate whether the ligand preferentially binds to one target or the other.

Methods described herein enable key features of the ligand, and the protein active site, and their interactions, to be visualized by providing a graphical user interface (GUI). Regions of hydrophobic enclosure, and special neutral-neutral and charged-charged hydrogen bonds, can be highlighted using color, texture, molecular surfaces, and other features available in the GUI. Visualization of these regions and structural motifs, which are responsible for enhanced binding affinity, facilitates the design of new, improved compounds, both with regard to enhancing binding affinity, and also with regard to retaining binding affinity while optimizing other features of the molecule.

Methods described herein enable a single, coherent approach, in which sampling algorithms and scoring function are optimized together.

One implementation of the invention provides all of the above advantages.

Other features and advantages of the invention are apparent from the following description, and from the claims.

BRIEF DESCRIPTION OF THE DRAWINGS

The file of this patent contains eight drawings executed in color. Copies of this patent with color drawings will be provided by the Patent and Trademark Office upon request and payment of the necessary fee.

Like reference numbers and designations in the various drawings indicate like elements.

DETAILED DESCRIPTION

Figure 1:
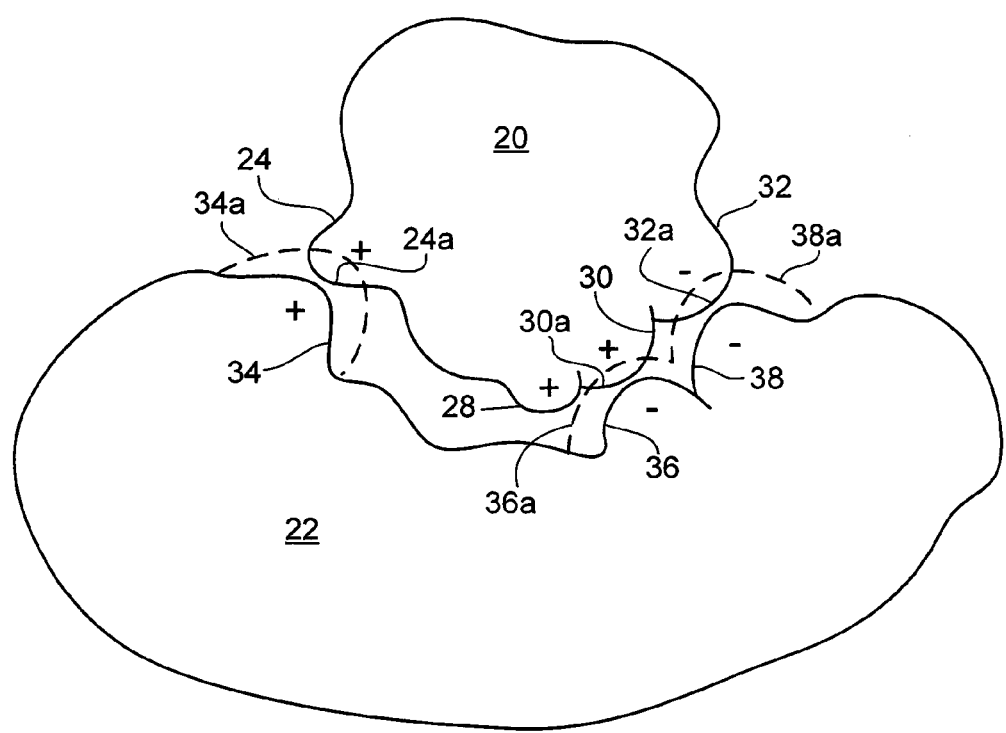
FIG. 1 is a block diagram.

As shown in FIG. 1, a block diagram of an exemplary molecular interaction geometry includes a first molecular entity 20 and a second molecular entity 22. In some cases, the first molecular entity 20 can be a drug candidate molecule (i.e., ligand), and the second molecular entity 22 can be a protein. The first molecular entity 20 includes atoms 24, 28, 30 and 32, with respective electrostatic charges (or partial charges) of positive, positive, positive, and negative. The second molecular entity 22 includes atoms 34, 36 and 38, with respective electrostatic charges (or partial charges) of positive, negative, and negative. Entity 20 is considered to be docked with entity 22. A protein 22-ligand 20 binding affinity, given as an input the docked structure shown in FIG. 1, can be calculated using a scoring function. A scoring function provides a way to calculate the binding affinity of a ligand in a protein receptor, given a sufficiently accurate structure of the complex. The calculated affinities can also be used to rank order ligands.

Effective use of a high precision scoring function typically requires an enhanced sampling methodology or the resulting docked structures are unable to evade large desolvation penalties, or to locate specific structural motifs that have been identified as contributing to enhanced binding affinity. Here, we assume that structures of this quality are generated in order to effectively apply the scoring function.

Our scoring function semi-quantitatively ranks an ability of candidate ligands to bind to a specified conformation of a protein receptor. Ligands that do not "fit" into the receptor, due to significant steric clashes, cannot be expected to achieve good scores, even if they bind effectively to an alternative conformation of the same receptor.

The definitions of receptor "conformation" and "fit" include a heuristic component. Some level of deviation of a true conformation induced by the ligand from the rigid receptor being docked into has to be allowed by a potential energy function used for docking; otherwise, a model would not be useful for virtual screening. The docking algorithm used to generate structures of the protein-ligand complex requires scaling of the van der Waals radii of the protein and/or ligand atoms, building in modest "induced fit" effects. There are many cases in which a reasonable degree of scaling will not enable the ligand to be docked correctly (e.g. if a side chain is in a rotamer state that is very different from that of the native protein-ligand complex and blocks the ligand atoms from occupying their preferred location in a binding pocket). There will always be situations on the borderline, but in practice we have found it possible to assign a great majority of cases of cross docking as either "fitting" or "not fitting."

The description herein focuses on complexes where the ligand fits appropriately into the receptor, as judged by an ability to make key hydrogen bonding and hydrophobic contacts, and achieve a reasonable root-mean-square-distance (RMSD), as compared to the native complex (or as obtained by analogy with the native complex of a related ligand).

Potential contributors to protein-ligand binding affinity include the following five contributors:

First, a term representing displacement of waters by the ligand from "hydrophobic regions" of the protein active site is a potential contributor. Liberating these waters into solution can result in lowering of the overall free energy. Waters in such regions may not be able to make their full complement of hydrogen bonds that would be available in solution. There can also be entropic considerations. If a water is restricted in mobility in a protein cavity, release into solvent will result in an entropy gain. Since one ligand releases many water molecules, this term will contribute favorably to the free energy.

Second, a term representing hydrogen bonding between the ligand and the protein is a potential contributor. If the hydrogen bonds formed by the ligand and protein are "better" in some fashion than those formed between each moiety and water, free energy gain will result. One reason that such a substitution can be favorable is if the water binding to the protein or ligand is otherwise poorly positioned to form additional hydrogen bonds. This term has some overlap with the term representing displacement of waters by the ligand from "hydrophobic regions" of the protein active site. Nevertheless, hydrogen bonding interactions have to be treated specifically, at least in an empirical scoring function of the type we consider here.

Third, a term representing desolvation effects can be a potential contributor(s). Groups in either the ligand or protein, formerly exposed to water, may become desolvated by being placed next to groups with which they cannot hydrogen bond. Such effects can only serve to reduce binding affinity, in contrast to the two terms described above.

Fourth, a term representing entropic effects due to restriction upon binding of the motion of flexible protein or ligand groups can be a potential contributor. As in the case of desolvation terms, such effects will serve exclusively to reduce binding affinity.

Fifth, specialized terms are needed to describe the interaction of the ligand with metal ions. This term can be added to other terms in the scoring function if a metal atom is present in the protein. Here we do not consider metal atoms. Embodiments of the invention are applicable to metal containing proteins, but the final, complete scoring function must be supplemented by a specialized term for metals as described above.

A large number of empirical scoring functions have been presented previously. While they differ from one another in detail, these prior scoring functions have similarities to each other. One such prior scoring function that we use as an example for comparison to our scoring function is Chem-Score. The ChemScore scoring function includes interactions between lipophilic atoms, hydrogen bond donors and acceptors, and hydrogen bond acceptors and metals, and an additional contribution based upon the number of restricted rotatable bonds of the ligand. When ChemScore is used, the position of hydrogens involved in hydrogen bonding is optimized with respect to the hydrogen bond energy (this is done for both protein and ligand donors).

ChemScore treats each of the four terms presented above (excluding the term specific to metal atoms) as follows.

ChemScore contains a hydrophobic atom-atom pair energy $E_{ph}$ term of the form:

$$E_{ph} = \sum_{ij} f(rij)$$

where 'i' and 'j' refer to (lipophilic) carbon atoms, and 'ƒ(rij)' is a linear function of the interatomic distance 'rij.' For rij less than the sum of the atomic Van der Waals (Vdw) radii plus 0.5 angstrom, 'ƒ' is 1.0. For larger distances ƒ ramps linearly to zero at 3 A beyond.

This $E_{ph}$ term heuristically represents displacement of waters from hydrophobic regions, which is most readily accomplished via lipophilic ligand atoms. Numerous close contacts between lipophilic ligand and protein atoms indicate that poorly solvated waters are successfully displaced by lipophilic atoms of the ligand, which themselves were previously exposed to water. The resulting segregation of lipophilic atoms, and concomitant release of waters from the active site to the bulk, lowers the free energy via the hydrophobic effect, which is approximately captured by the scoring function above. Terms involving contact between hydrophobic surfaces of the protein and ligand, while differing in details, essentially attempt to measure the same free energy change via a very similar type of approximation.

ChemScore evaluates protein-ligand hydrogen bond quality based on geometric criteria, but does not distinguish between different types of hydrogen bonds, or differing protein environments.

ChemScore does not treat desolvation effects.

ChemScore uses a simple rotatable bond term to treat conformation entropy effects on the ligand.

Our scoring function begins from the terms used in ChemScore discussed above, although their detailed parametrization is specific to our scoring function. Our scoring function qualitatively revises the hydrophobic term and hydrogen bonding terms. We have also developed desolvation terms. The desolvation terms must be included to calculate the total binding affinity.

Our scoring function includes an improved model of hydrophobic interactions that we refer to as "hydrophobic enclosure." The "standard" atom-atom pair function as illustrated in ChemScore, $E_{PH}$, from which we begin, assigns a score to a lipophilic ligand atom based on the distance distribution of lipophilic protein atom neighbors. This clearly captures a significant component of the physics of the hydrophobic component of ligand binding. Displacement of waters from areas with many lipophilic protein atoms nearby is likely worth more in free energy than displacement from areas with fewer such atoms. As one example, it is clear that if a ligand is placed in an active site cavity, as opposed to on the surface of the protein, the lipophilic atoms of the ligand are likely to receive better scores. If they are located in a "hydrophobic pocket" of the protein, the scores should be better than in a location surrounded primarily by polar or charged groups. However, a scoring function dependent only upon distance distribution is not sensitive to the details of the local geometry of the protein atoms relative to the ligand lipophilic atom in question.

Figure 2A:
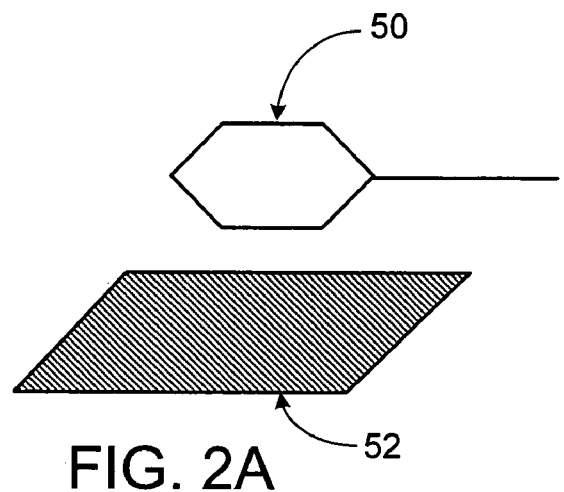
FIG. 2 is a diagram of a ligand group interacting with two distinct hydrophobic environments.
Figure 2B:
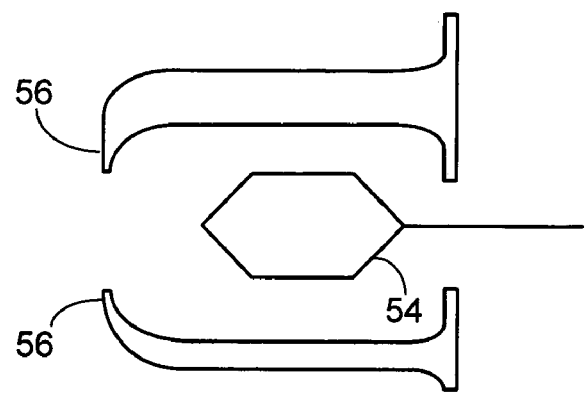

As an example, consider two model distributions shown in FIG. 2. In one case (A), a ligand atom 50 is placed at a hydrophobic "wall." Lipophilic protein atoms 52 are only on one "side" of the hydrophobic atom. In the second case (B), the lipophilic ligand atom 54 is placed into a tight pocket, with lipophilic protein atoms 56 on two (or three) "sides" of the ligand atom 56. By adjusting the distance parameters and numbers of relevant protein atoms, it is possible to construct two models which yield identical scores for any atom-atom pair term (regardless of coefficients) for structures A and B. The question is whether the contribution of the atom to the free energy of binding in constructions A and B should be identical under the stipulated conditions.

The answer depends principally upon the free energy to be gained by displacing a water molecule at a given location in a protein cavity, which depends upon how successfully that water is able to satisfy its hydrogen bonding requirements at that location. In an extreme case, where a single water molecule is placed in a protein cavity that can accommodate only one water, and is surrounded on all sides by lipophilic atoms that cannot make hydrogen bonds, the free energy of transfer to bulk via displacement by a hydrophobic ligand group is clearly favorable, and it is not clear that a water molecule would occupy such a cavity in preference to leaving a vacuum, despite the statistical terms favoring occupancy. This is a very rare situation that is not particularly relevant to binding a large ligand, whereas the examples in FIG. 2 are quite common.

We have carried out a large number of computational experiments involving modifications of the hydrophobic scoring term (in our scoring function) designed to discriminate between different geometrical protein environments. A criterion for success in these experiments is the ability of any proposed hydrophobic scoring term to fit a wide range of experimental binding free energy data and yield good predictions for enrichment studies. Our results are described below in the following paragraphs.

Ligand lipophilic atoms must be considered in groups, as opposed to individually. The free energy of water molecules in a protein cavity is adversely affected beyond the norm primarily when placed in a hydrophobic microenvironment extended over the dimension of several atoms. If there are individual isolated hydrophobic contacts, the water will typically be able to make its complement of hydrogen bonds anyway, by avoiding these contacts and using neighboring waters as partners. We have set a minimum group size of connected lipophilic ligand atoms at three.

When a group of lipophilic ligand atoms is enclosed on two sides (at a 180 degree angle) by lipophilic protein atoms, our method hypothesizes that this type of structure contributes to the binding free energy beyond what is encoded in the atom-atom pair term. We refer to this situation as "hydrophobic enclosure" of the ligand. The atom-atom pair term is fit to a huge, heterogeneous data set and is dominated by individual lipophilic ligand atoms in an "average" environment, i.e., not in a group residing in a specially configured hydrophobic region of the protein. Our scoring function terms are designed to capture favorable deviations from this average, which represent specific molecular recognition motifs. That is, placing an appropriate hydrophobic ligand group within the specified protein region leads to substantial increases in potency beyond the average for such a group, of the type that are typically targets of medicinal chemistry optimization programs.

Figure 3:
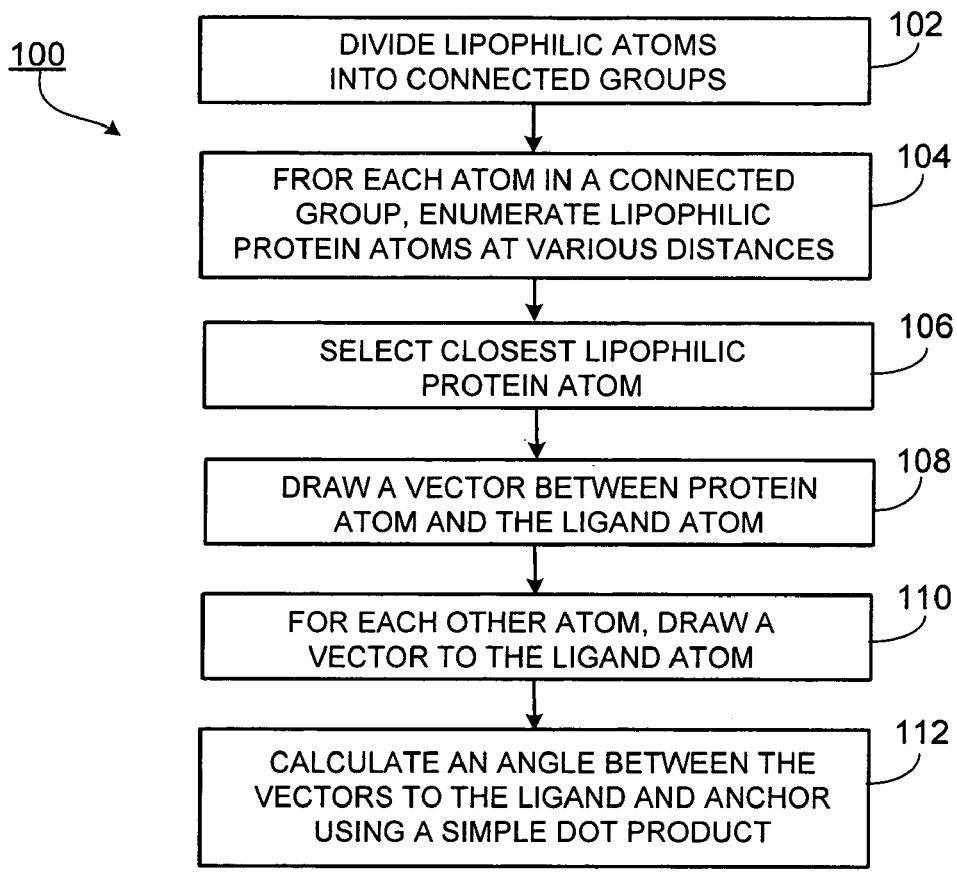
FIG. 3 is a flow diagram.

As shown in FIG. 3, a hydrophobic packing score process 100 includes dividing (102) lipophilic atoms into connected groups.

For each atom in a connected group, process 100 enumerates (104) lipophilic protein atoms at various distances. Process 100 selects (106) the closest lipophilic protein atom, and draws (108) a vector between it and the ligand atom. This is referred to as an "anchor" atom.

All other atoms on the list are taken, one at a time, and for each atom, process 100 draws (110) a vector to the ligand atom, and calculates (112) an angle between the vectors to the ligand and anchor atoms, using a simple dot product algorithm. In order to be considered on the "other side" of the anchor atom, the angle between the vector must exceed some value (which depends on distance—the further away, the closer to 180 degrees the angle has to be). If the angle is 0 degrees, then the vectors are parallel, and the atom is on the "same side." If the angle is 90 degrees, the vectors are at right angles and the atom is "at right angles" to the anchor. If the angle is 180 degrees, the atom is exactly on the "other side" and that is what leads to an especially bad environment for waters. This is supported by molecular dynamics simulations of waters at hydrophobic surfaces of varying curvature, and also by common sense geometrical arguments.

Process 100 assigns each atom a score based on the number of total lipophilic contacts (with a distance cutoff), designated the contact score, and a weighting depending upon the angle term. If, for example, no atom is more than 90 degrees away from the anchor, the angle term is zero and the atom contributes zero to the group "special hydrophobic" term. Process 100 adds scores of all of the atoms in the group, and the total is the score for that group. A detailed mathematical description of process 100 is provided in Appendix I.

If the score is greater than 4.5 kcal/mole, process 100 caps the term at this value. This is an empirical determination based on analyzing many different test cases and comparing the results with experimental data. If one region of this type is very large, leading to a score greater than 4.5, there is probably some ability of the water molecules to compensate by interacting with each other—smaller regions have more difficulty doing this, the capping term compensates for that effect.

Figure 4:
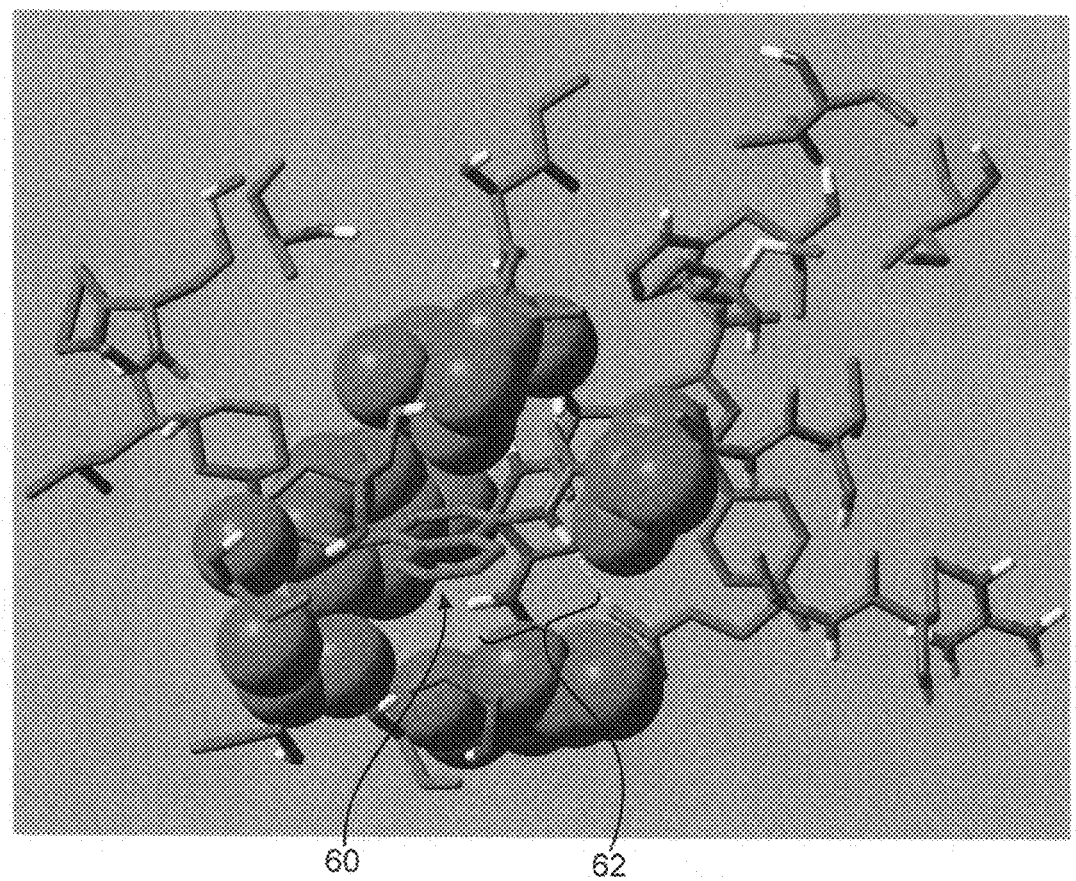
FIG. 4 illustrates Boehringer active ligand BIRB796 binding to the DFG-out conformation of p38 MAP kinase (pdb 1kv2).

One particular experimental illustration of the binding affinity gain if a large hydrophobic group (rings in both cases) is placed into a pocket in which lipophilic protein atoms are present on both sides of the pocket is shown in FIG. 4. The napthyl group 60 of this very tight binder was shown to improve the binding relative to just a phenyl group by a factor of 21. The napthyl group 60 is required to fully occupy the phobic pocket 62 depicted in FIG. 4.

As described above, we refer to the surrounding of lipophilic atoms or groups of the ligand by lipophilic protein atoms as a "hydrophobic enclosure." Proper treatment of hydrophobic enclosure is a key to discrimination of highly and weakly potent binding motifs and compounds. Detailed optimization of the numerical criteria for recognizing hydrophobic enclosure, and assigning a specific contribution to the binding affinity for each motif, is important if one desires to develop methods with predictive capability, and we have tuned the terms of our scoring function using a large set of experimental data.

The above describes a particular method for detecting hydrophobic enclosure, starting from a predicted structure of a protein-ligand complex. Other methods can be constructed to achieve nearly the same results with regard to computation of the contribution of enclosure to binding affinity.

The method that is described above for detection of hydrophobic enclosure is based on using the docked protein-ligand complex as a starting point for the enclosure calculation. Another approach is to start with an apoprotein structure, i.e., the protein in the absence of any ligand, and perform a simulation of the protein using explicit water molecules as the solvent. One can detect whether there were any locations in the system in which water molecules are having difficulty forming their full complement of hydrogen bonds due to the presence of hydrophobic enclosure by the protein, and label these regions as favorable for occupancy by appropriate ligand groups. This approach uses the hydrogen bonding characteristics of water molecules in specific locations to detect enclosure, as opposed to inferring such characteristics from the docked protein-ligand complex. Based on such simulations, one can construct terms of a scoring function that reward occupancy of the appropriate protein regions (e.g., in a grid based scheme).

Our scoring function includes a term representing an improved model of protein-ligand hydrogen bonding. In developing a refined model of hydrogen bonding, we divide hydrogen bonds into three types: neutral-neutral; neutral-charged; and charged-charged. The analysis of each type of hydrogen bonding is different, due to issues associated with the long range solvation energy (Born energy) of charged groups. An initial step is to assign different default values (assuming optimal geometric features) to each of these three different types of hydrogen bonds. The default values that we assign are: neutral-neutral, 1 kcal/mole; neutral-charged, 0.5 kcal/mole; and charged-charged 0.0 kcal/mole. These assignments are based on a combination of empirical observation (best fitting to reported binding affinities of a wide range of Protein Data Bank (PDB) complexes) and physical reasoning.

A rationale for rewarding protein-ligand hydrogen bonds at all is subtle because any such hydrogen bonds are replacing hydrogen bonds that the protein and ligand are making with water. The net number of total hydrogen bonds on average will remain the same in the bound complex as compared to solution. However, the liberation of waters to the bulk results in an increase in entropy, and liberation of waters around a polar group requires a protein-ligand hydrogen bond. This analysis is most plausible when both groups are neutral. The formation of a salt bridge between protein and ligand involves very different types of hydrogen bonding from what is in solution. The thermodynamics of salt bridge formation has been studied in proteins, and depends upon many factors such as the degree of solvent exposure. The default value of zero that we assign is based on the presence of many protein-ligand complexes in the PDB with very low binding affinities in which salt bridges are formed. Special features of a salt bridge are required in order for this type of structure to contribute to binding affinity in our scoring function. Finally, the charged-neutral default value represents an interpolation between the neutral-neutral and charged-charged value, which appears to be consistent with the empirical data.

Hydrogen bond scores are diminished from their default values as the geometry deviates from an ideal hydrogen bonding geometry, based on both the angles between the donor and acceptor atoms and the distance. A detailed description is provided in Appendix II. We describe below specialized structures in which hydrogen bonds are assigned additional increments of binding affinity (designated "rewards") that are significantly in excess of the default values. These situations can arise for neutral-neutral, or charge-charge, hydrogen bonds, but not for charge-neutral hydrogen bonds. The exclusion of charge-neutral hydrogen bond special rewards has been driven by the failure to identify motifs of this type that can yield better agreement with the experimental data.

We now describe particular types of neutral-neutral hydrogen bonds that have been identified, based on both theoretical and empirical considerations, as making exceptional contributions to the binding affinity. Such "special" hydrogen bonds represent key molecular recognition motifs, and are found in many if not most pharmaceutical targets. Targeting such motifs is a central strategy in increasing the potency and specificity of medicinal compounds. The development of an automated scoring function capable of properly assigning binding affinity to structures of this type (as opposed to after the fact rationalization of "important" hydrogen bonds in each individual target) is a major objective in the development of empirical scoring functions, enabling a dramatic improvement in both qualitative and quantitative prediction capability.

A key idea with respect to important hydrogen bonds is to locate positions in the protein cavity where the waters forming a hydrogen bond to a polar group would have particular difficulty making their normal complement of additional hydrogen bonds. Forming a hydrogen bond with a protein atom imposes nontrivial geometrical constraints on the water molecule. This is the basis for the default hydrogen bond score. But such constraints become more problematic when the remaining environment of the water molecule is challenging with regard to making additional hydrogen bonds.

Our analysis of hydrophobic interactions suggests that the environment will become qualitatively more challenging if the water molecule has hydrophobic protein atoms on two sides (as opposed to only one) and also if there are few neighboring waters with the capability to readjust themselves to the constrained geometry of the protein-ligand hydrogen bond. We identify geometries of this type by using a variant of the method described above for detecting hydrophobic enclosure. Replacement of such a water by the ligand is particularly favorable if the donor or acceptor atom of the ligand achieves its full complement of hydrogen bonds by making the single targeted hydrogen bond with the protein group in question, so that satisfaction of additional hydrogen bonds is not an issue.

Figure 5:
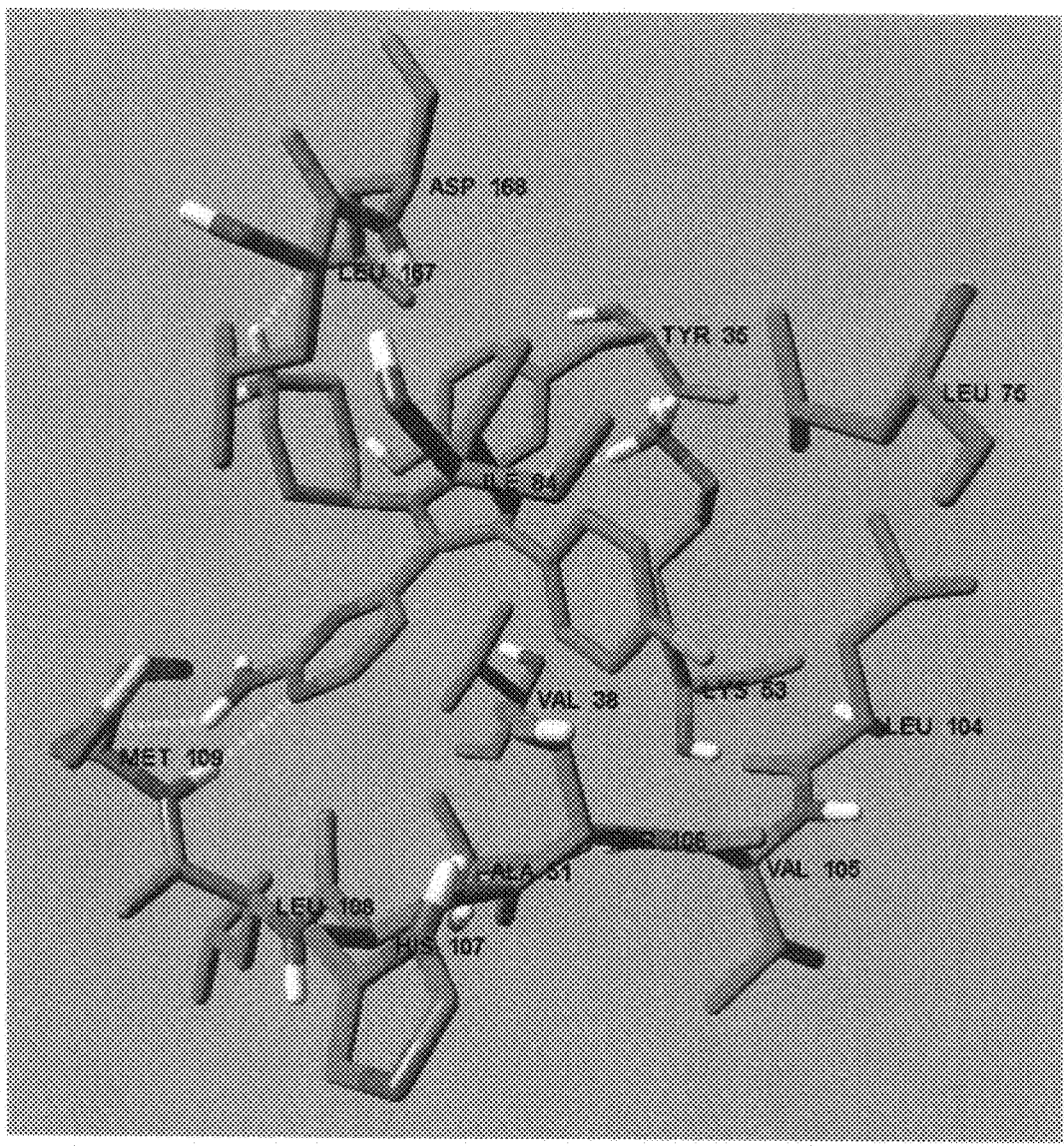
FIG. 5 depicts SB220025 binding to p38 MAP kinase.

An example of a suitable group is a planar nitrogen in an aromatic ring, binding for example to a protein N-H backbone group. An illustrative example of a structure of this type, observed to be essential to achieving high potency experimentally, is shown in FIG. 5; the system depicted is SB220025 binding to p38 MAP kinase. The Met 109 hydrogen bond is known as being important to potency, as are analogous hydrogen bonds in other kinases. The scoring function term described above enables such hydrogen bonds to be detected automatically, and in advance of experimental measurement. Of equal importance, false positives, which superficially share some characteristics of the required structural motif but are lacking a key component, can be rejected automatically as well. Rejection of false positives has been optimized by running a given variant of the scoring function, identifying high scoring database ligands with special hydrogen bonds in locations not seen in known actives, examining the resulting structure, and altering parameters to eliminate the reward for the particular test cases in question.

A process 200 for detecting a single hydrogen bond in a hydrophobic environment includes the following. The donor or acceptor atom must be in a ring with the exception of nitrogen, which is allowed to be a non-ring atom. If the ligand atom is a donor group, then all other donors of the group (e.g., two hydrogens of $NH_2$) must be H-bonded to the protein. Only backbone protein atoms can participate in this type of special H bond. The relevant protein donor or acceptor atom in the apoprotein structure (i.e., the structure with no ligand present) must have fewer than 3 first shell solvating waters. The number of waters in the first shell is determined using a grid based program for adding waters to a protein structure or protein-ligand complex (water addition code). If these criteria are met, the sum of the angular factor of the hydrophobic packing score is made by summing over the ligand H-bonded heavy atom and the carbon atoms attached to this ligand atom. The specialized hydrophobic packing term used in this sum contains only the angular weight of the hydrophobic packing score described in process 100 and not the contact weight. If the absolute phobic packing sum is above a cutoff, the H-bond is considered to be in a hydrophobically constrained environment and a special H bond reward of −1.5 kcal/m is applied to this H bond. In some instances, it is found that a small perturbation of the ligand can move the specialized hydrophobic packing term above the cutoff. Therefore, if the term is initially below the cutoff, small rigid body perturbations of the ligand are made of 0.3 A in magnitude. At each perturbed geometry the term is recalculated and if at some geometry the term exceeds the cutoff, a reward is applied. This helps to avoid the discontinuities inherent in the use of a cutoff.

Process 200 identifies a structure in which a single hydrogen bond should be assigned a "special" reward. A second situation occurs when there are multiple correlated hydrogen bonds between the protein and the ligand. Organization of water molecules to solvate effectively a structure of this type in the confined geometry of the active site can be even more problematic than the situation described above. This occurs only if the waters involved in such solvation are in a challenging hydrophobic environment, with hydrophobic groups on two sides. The coupling of the special hydrogen bond identification with the hydrophobic enclosure motif is critical if false positives are to be rejected. Correlated hydrogen bonds are routinely formed in docking with for example highly solvent exposed backbone pairs, but there is no evidence from the experimental data that such structures contribute to enhanced potency in any known medicinal chemistry series. Details as to the assignment of special rewards for systems with two and three correlated hydrogen bonds are described in Appendix II.

Multiple hydrogen bonds are defined with respect to the ligand as a donor/acceptor, donor/donor, or acceptor/acceptor pair of atoms (referred to as 'ligand atom pair'), which are separated by no more than 1 rotatable bond (OH groups count as non-rotatable in this calculation). Several restrictions on the types of pairs that can be considered are made as shown in the following table.

---

1) Skip poor quality H bonds (<0.05 HB pair score)
2) Do not include pairs involving the same neutral protein atom.
3) Skip pairs involved in a salt bridge if the electrostatic potential at either ligand atom is not below a cutoff.
4) Skip salt bridge pairs if either protein atom is involved in a protein—protein salt bridge.
5) Skip ligand donor/donor pairs which come from $NH\_x$ x >= 2 groups. N non-ring and with zero formal charge.
6) Skip formally charged protein atoms with more than 8 second shell waters in the unligated state.
7) Skip charged-neutral H bonds unless the protein atom is in a salt bridge.
8) Skip pairs of different neutral acceptor atoms on the ligand.
9) Neutral H bond pairs must satisfy ring atom and phobicity environment checks.
10) Skip ligand OH to protein H bonds if the protein atom has zero formal charge.

---

If the ligand atoms of the pair individually have zero net formal charge, then they must satisfy the following hydrophobicity check and criteria to achieve a special H bond reward. First, the ligand atoms must be part of the same ring or can be non-ring atoms only if directly connected to the same ring. Assuming the pair satisfies these restrictions, the hydrophobicity of the H bond region is detected in a manner similar to that for a single H bond. A sum of the hydrophobic packing score described above is made using the pair of H bonding ligand heavy atoms and the ring atoms directly connected to the ligand pair atoms. If a ligand atom of the pair is not a ring atom but connected to a ring, the sum includes atoms of the ring which are next neighbors to the non-ring ligand atom. If the described absolute phobic sum is above a cutoff, the H bonded pair is given a special reward of 3 kcal/m. Double counting of pair and single special H bonds is avoided by looking for pairs first and excluding any rewarded H bonds found in the pair list from the single H bond reward list.

The special H bond rewards are scaled down linearly with the quality of the H bond. The H bond quality is measured in the sense of the pair H bond score using the donor/acceptor distance and the angle made by the donor-heavy-atom —H vector and the H-acceptor vector. For ligand acceptor atoms in rings a check is made for the extent to which the acceptor lone pair vector is aligned with the donor-heavy-atom —H vector. A detailed description as to how this is accomplished mathematically in our current implementation is provided in Appendix 2.

Figure 6:
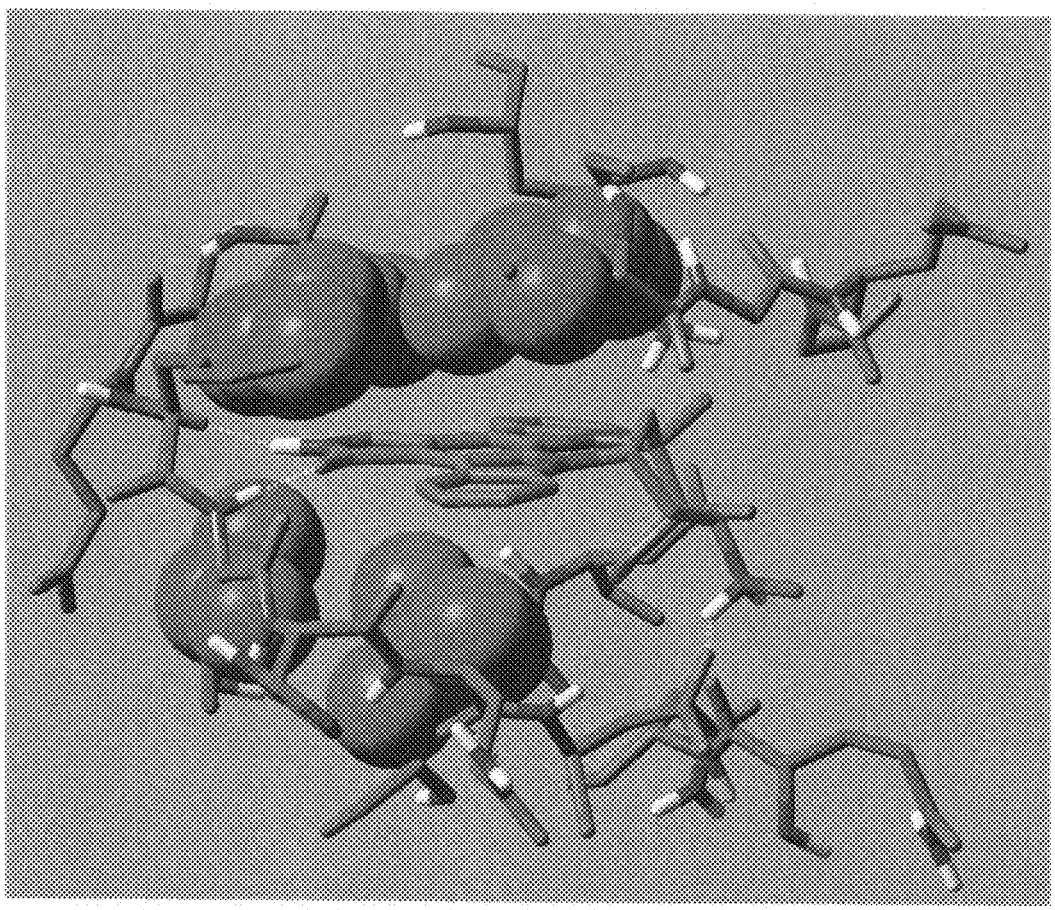
FIG. 6 illustrates Staurosporine inhibitor of CDK-2 (pdb 1aq1) binds via a special hydrophobically surrounded H bond pair at the backbone (XP reward 3 kc/m) as well as filling the hydrophobic pocket with the fused ring (reward 4.5 kc/m).
Figure 7:
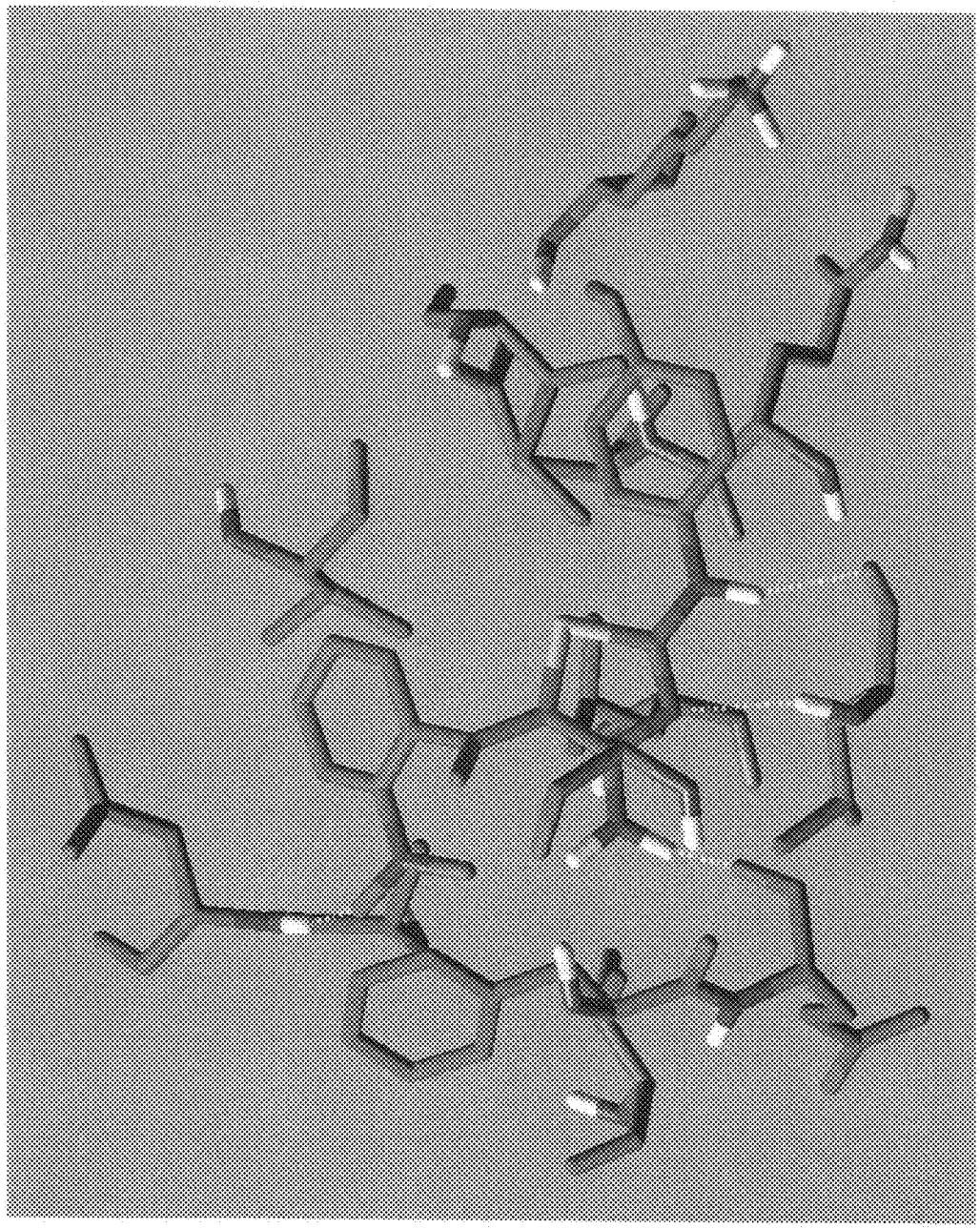
FIG. 7 illustrates CDK-2 inhibitor cgp6047 cross docked into pdb entry 1aq1.

We have identified a substantial number of protein-ligand complexes in which motifs containing two or three correlated hydrogen bonds, which satisfy the above criteria (including the requisite hydrophobic enclosure), are present. A number of examples are shown below. The first, which is shown in FIG. 6, depicts staurosporine bound to the CDK2. This type of correlated pair is found in a number of other kinases as well. Some of the CDK2 actives, such as cgp60474, make three correlated hydrogen bonds; this structure is shown in FIG. 7.

Figure 8:
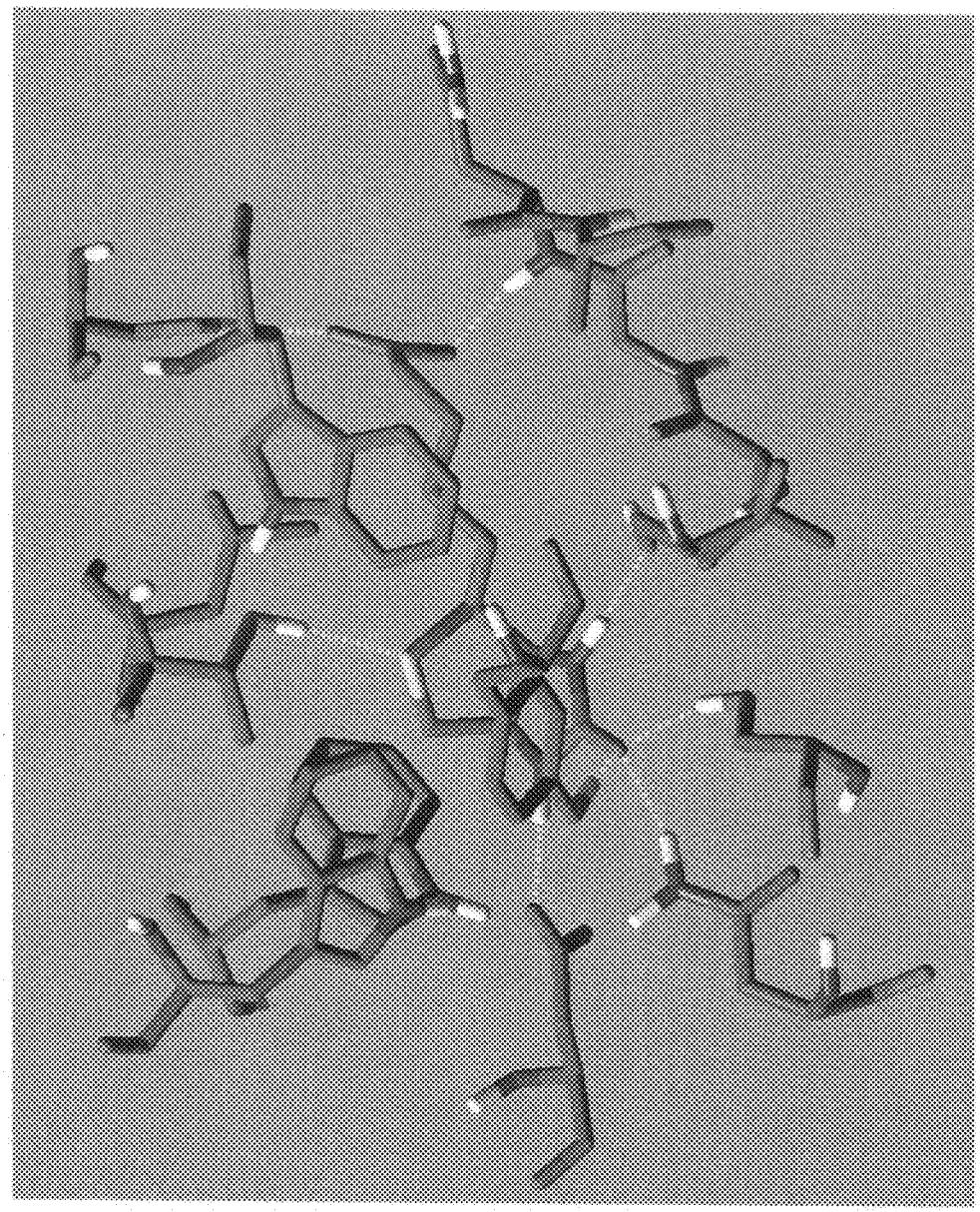
FIG. 8 illustrates Streptavidin in biotin (pdb 1stp). Both special hydrogen bonds in this complex, and hydrophobic enclosure of the hydrogen bonding region, are shown.

FIG. 8 shows a second example with streptavidin bound to biotin. Here three correlated hydrogen bonds occur in a hydrophobically enclosed region. Up to the present time, no empirical scoring function has explained the exceptionally large binding affinity of streptavidin in biotin. Once the triple, enclosed hydrogen bonding motif is recognized and assigned an appropriate score, the deviation between calculated and experimental binding affinity, using a docked structure, is only 1.5 kcal/mole.

Figure 9:
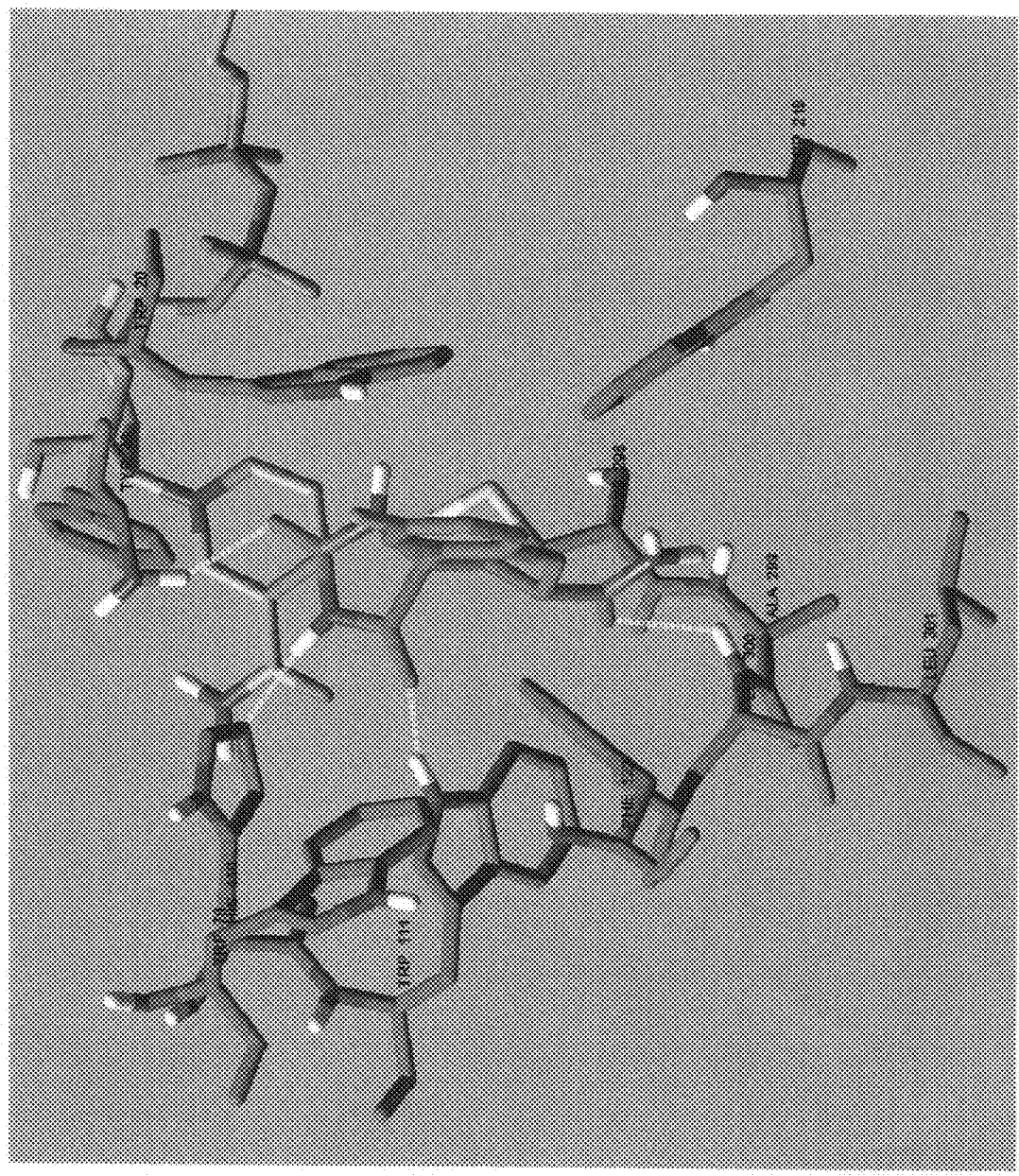
FIG. 9 illustrates HIV-RT pocket (pdb 1rt1) bound with inhibitor via a special hydrophobically surrounded H bond to the backbone (1.5 kc/m reward) and hydrophobic packing of the ligand aromatic ring (4.5 kc/m reward).

A third, different example, shown in FIG. 9, is a fiderestat inhibitor bound to the lef3 structure of aldose reductase, which also exhibits a triple correlated hydrogen bond. The large additional score associated with this hydrogen bond is necessary to explain why this compound stands out (low nanomolar binding affinity experimentally) from among the large number of ligands that achieve large hydrophobic scores (in a virtual screening experiment) in the highly hydrophobic pocket of the lef3 native complex.

The combination of hydrophobic enclosure with 1 to 3 correctly positioned hydrogen bonds is characteristic of every "special" neutral-neutral hydrogen bond that we have identified in our studies of various pharmaceutically relevant targets. However, additional characteristics are required in order to eliminate false positives. In particular, if the hydrogen bond partner in the protein is highly solvent exposed, then the formation of a structure capable of solvating the group in question, while still allowing the waters involved to form a suitable number of additional hydrogen bonds, becomes easier. Thus, we require that the protein group(s) involved in the special hydrogen bond(s) have a limited number of waters in the first or second shell. The number of such waters are determined using the water addition method discussed above.

The magnitude of the rewards associated with the special hydrogen bonds has been determined by optimization against a large experimental database, containing a significant number of examples of each type of structure. Values are given in the table below.

| H-bond moiety | Reward |
| --- | --- |
| Single bond to ring in phobic environs | 1.5 kc/m |
| Neutral Pair in phobic environs | 3.0 kc/m |

We have identified the following features that signal enhancement of charge-charge hydrogen bonds.

(1) Number of waters surrounding the protein component of the salt bridge. Charged groups that are fully exposed to solvent are unlikely to participate in enhanced charge-charge hydrogen bonding. The cost of displacing the solvent is too large.

(2) Number of charge-charge hydrogen bonds made by the charged ligand group. We have observed that there are three different types of salt bridge structures formed:

(a) Monodentate (single hydrogen bond) between the ligand group and one protein group.

Figure 10:
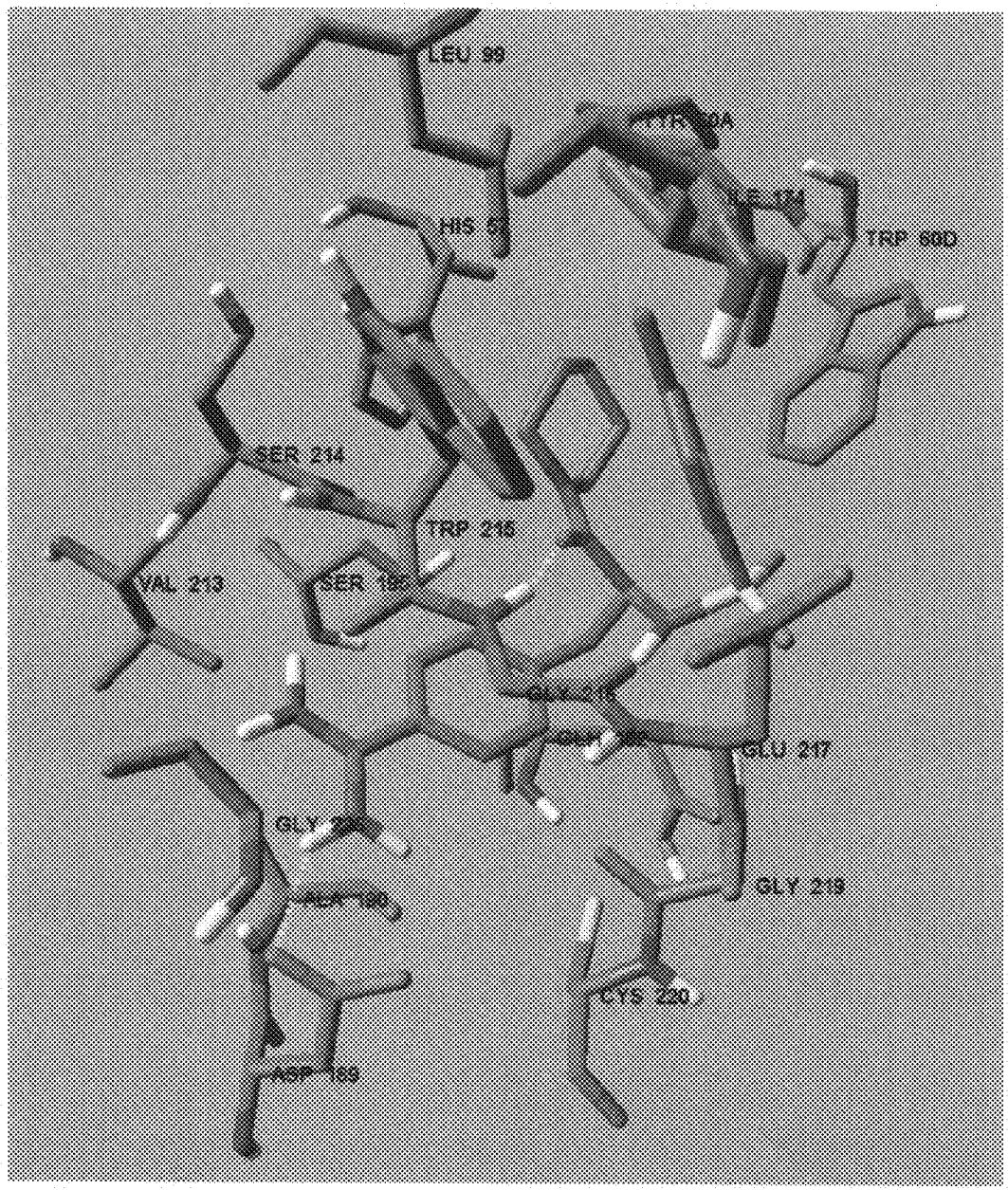
FIG. 10 illustrates a Thrombin inhibitor (pdb 1ett) bound via a salt bridge to recessed ASP_189.

(b) Bidentate (two hydrogen bonds) between the ligand group and one protein group. An example of a bidentate salt bridge in thrombin, between a positively charged amine group and a recessed carboxylate in the relevant specificity pocket, is shown in FIG. 10.

(c) Hydrogen bonds of one ligand group to two different protein groups. This requires having two like charged protein groups in close proximity. This type of structure, which presumably creates strain energy in the protein, occurs frequently. It appears to be a special type of molecular recognition motif which develops via evolutionary pressure.

Figure 11:
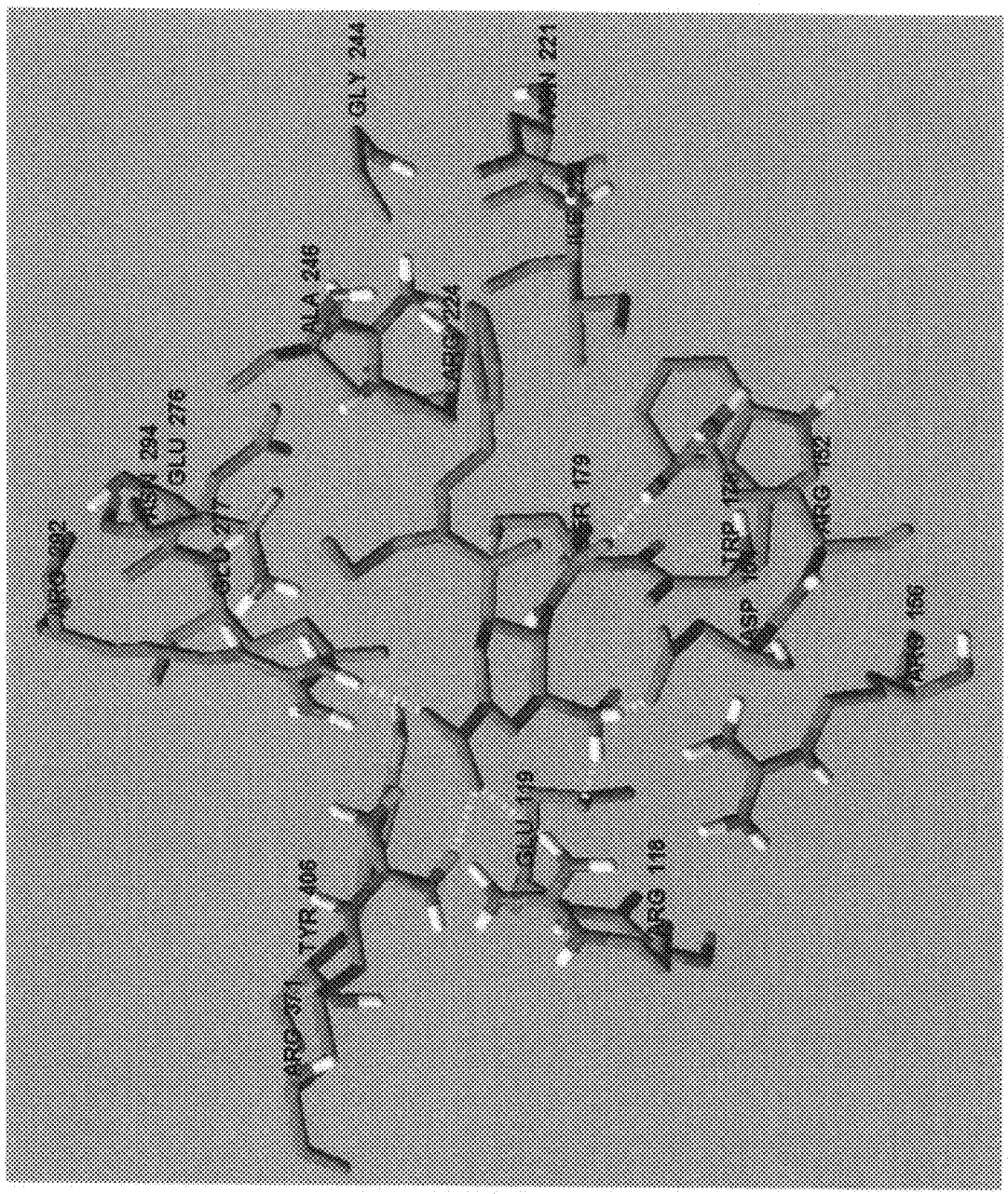
FIG. 11 illustrates a ligand bound to neuramididase protein (pdb 1bji).

FIG. 11 illustrates an example showing the ligand Gr217029 binding to the term N9 influenza virus version (pdb code 1bji) of the neuramididase receptor. The distance between carboxylate oxygens is only 4.5 Å in this case.

Both empirical data and physical chemical reasoning suggest that hydrogen bonds of type (c), above, provide more stabilization energy than those of (b), which in turn provides more stabilization energy than those of (a). Unless condition (1) is properly satisfied, none of the three structures is likely to be favorable from a free energy point of view. It is the combination of restricted water access for the protein group, and an exceptionally strong electrostatic interaction between the ligand and protein group, that creates a molecular recognition motif.

(3) For zwitterions, a principal reason that a default value for charge-charge hydrogen bonds is set to zero is that, in forming a salt bridge, both the protein and ligand must surrender long range contributions to Born energy (i.e., beyond the first shell). Satisfying the first shell complement of hydrogen bonds is quite possible when forming a salt bridge, but the replacement of bulk water with the protein, or bound waters, clearly reduces the possible dielectric response to the ion. For a monovalent ion, the Coulomb field falls off approximately 1/r, so long range effects (at least out to the second shell) make a nontrivial contribution to the total solvation free energy. However, for a zwitterion, the fields from the positive and negative charges to some extent cancel at long range (how much depends upon the separation of the two charged groups), yielding a dipolar field for which the second (and higher) shell contributions to the solvation free energy are significantly reduced. Thus, formation of two salt bridges by the zwitterion, particularly if the two charged moieties are spatially proximate, should be more favorable than binding a single ion. An example of a zwitterion binding in this fashion is shown in FIG. 11.

(4) We distinguish between cases where the ligand is positively charged and the protein negatively charged, and vice versa.

(5) Strength of the electrostatic field at the ligand. In order to receive enhanced binding affinity for a salt bridge, the site at which the ligand charge is placed must be electrostatically favorable. We sum the screened electrostatic field at the ligand site, and impose cutoffs for assigning rewards based on empirical optimization over our suite of test cases. These cutoffs help to reduce the number of false positives receiving special charge-charge rewards.

The following table enumerates the various special charge-charge rewards, both with regard to criteria (based on the five categories discussed above) and numerical values assigned to the rewards. The latter have been optimized based on fitting to our entire test suite.

| Charge Interaction | Reward |
|---|---|
| Charged ligand atom in low electrostatic potential environs. | 1.5 kcal/m |

-continued

| Charge Interaction | Reward |
|---|---|
| Zwitterion configuration, range of rewards increasing with electrostatic attraction | 3.0 to 4.7 kcal/m |
| Positive ligand group binding to weakly solvated negative protein group. | 0.5 kcal/m |
| Ligand co2— group H bound to multiple proximate positive protein residues | 1.0 kcal/m |
| Salt bridge pair in low solvation environs (less than 9 second shell waters about pre-ligated charge protein atom) | 2.0 kcal/m |

The following table displays the scoring function active scores for a series of Glur2 receptors compared to the experimental binding energies.

| Ligand | Our Score | ΔG_(kc/m) |
|---|---|---|
| 1ftl | 8.1 | 8.3 |
| 1pwr | 10.5 | 13.0 |
| 1ftj | 9.3 | 8.5 |
| 1mm7 | 11.0 | 12.7 |
| 1mqi | 12.0 | 11.9 |
| 1ftm | 10.5 | 8.8 |
| 1n0t | 7.0 | 5.7 |
| 1ftl | 8.1 | 8.3 |
| 1m5b | 10.8 | 9.3 |
| 1m5c | 9.5 | 9.3 |
| 1m5e | 9.1 | 6.3 |

Glu2 receptor is a system, along with neuramididase, for which electrostatic interactions are particularly important, and thus provides an important contribution to the training set for these types of interactions.

It has been observed empirically that larger ligands tend to be favored by most scoring algorithms. We have implemented two types of terms based on these observations:

(1) A reward is assigned to smaller ligands based on their mass. The term we use is linear and covers the mass range from 300 to 450. Below 300, all ligands receive the maximum reward (1 kcal/mole); above 450, all ligands receive 0.

(2) Terms recognizing aromatic stacking, and pi-cation interactions, which have been hypothesized for many years to play a significant role in protein-ligand binding affinities for specific complexes possessing one or both of these motifs. We have included several systems in this category in our data set (e.g., fxa, acetylcholinesterase) and developed a geometrical description of each type of interaction, optimized to include active compounds, and eliminate false positives. Values for the various interactions were assigned in the course of the enrichment and binding affinity studies.

Two more scoring terms are derived from a phobic/polar surface 'site map' of the protein. The first attractive 'polar phobic' term rewards polar atoms in phobic regions of the active site map. Phobic regions are determined in this method as points on a grid with favorable vdW interactions and low electric fields from the protein. Polar atoms are non-carbon non-acceptor non-donor atoms. This attractive term is typically on the order of 0.5 kcal/m so does not contribute significantly to the average. A repulsive site-map 'phobic repulsion' score penalizes phobic ligand atoms found in regions of the protein with high electric fields. These regions are presumed in this method to be occupied by water. This term also contributes at the level of 0.3 kcal/m on average and less frequently than the polar phobic term.

The following equation incorporates all the terms used to calculate the components of our scoring function which favor binding. We have optimized these terms based on experimental binding affinities and crystal structures.

$$E{bind} = E{pho\_pack} + E{electro} + E{HB\_spec} + E{HB\_pr} + E{pho\_pr} + E{pi}$$

where $E_{pho\_pack}$ is the phobic packing/enclosure term; $E_{electro}$ contains any of the electrostatic rewards; $E_{HB\_spec}$ contains rewards for H bonds in phobic regions; $E_{HB\_pr}$ is the standard H bond pair term; $E_{pI}$ contains the pi-cation and pi stacking terms; and finally $E_{pho\_pr}$ is the standard lipophilic pair term. As indicated above, this term must be supplemented with desolvation and entropic terms to calculate the final score for the binding affinity, which is reported below. Efficacy of our method is based on calculation of binding affinities for a set of protein-ligand complexes in the PDB, using docked poses (thus showing that good results for prediction of binding affinity can be obtained with docked poses as opposed to experimental structures). The table below presents results for our scoring function for structural RMSDs from the binding affinities of the various complexes discussed herein, wherein "XP Score" refers to results obtained from our scoring function and the "SP Score" represents scores using an older scoring function for comparison. Experimental binding affinities are included in the table where available.

| PDB entry | XP Score | ΔG_exp | XP RMS | SP Score | ΔG_exp | SP RMS |
|---|---|---|---|---|---|---|
| 1aaq | −11.1 | −10.8 | 12.1* | −12 | −10.8 | 1.6 |
| 1abe | −8.9 | −9.2 | 0.3 | −11.5 | −9.2 | 0.4 |
| 1abf | −6.1 | −7.2 | 0.1 | −11.8 | −7.2 | 0.1 |
| 1acj | −9.8 | −10 | 2.8 | −7.6 | −10 | 4.6 |
| 1acm | −13.7 | — | 0.4 | −15.4 | — | 0.3 |
| 1aco | −4.2 | — | 0.3 | −9.7 | — | 1 |
| 1add | −11.1 | −9.2 | 0.5 | −9.3 | −9.2 | 0.6 |
| 1adf | −9.1 | −6.2 | 4.5 | −13.7 | −6.2 | 2.9 |
| 1aha | −8.6 | — | 0.2 | −7.9 | — | 0.1 |
| 1ake | −22 | — | 1.3 | −10.3 | — | 2.8 |
| 1apb | −7.8 | −7.9 | 0.1 | −11.6 | −7.9 | 0.1 |
| 1apt | −12.3 | −12.8 | 0.9 | −11 | −12.8 | 0.6 |
| 1apu | −9.8 | −10.5 | 1.3 | −8.8 | −10.5 | 1 |
| 1apv | −11.7 | −11.3 | 0.7 | −9.8 | −11.3 | 0.4 |
| 1apw | −11.2 | −10.9 | 1 | −9.6 | −10.9 | 0.3 |
| 1atl | −10.6 | — | 0.9 | −8.2 | — | 2.4 |
| 1avd | −17.2 | — | 0.6 | −10.2 | — | 0.5 |
| 1azm | −5.1 | — | 1.9 | −6.3 | — | 1.5 |
| 1b6j | −12.1 | — | 2.8 | −16 | — | 3.1 |
| 1b6k | −14.6 | — | 1.3 | −13.9 | — | 0.7 |
| 1b6l | −10.5 | — | 1.1 | −11.2 | — | 0.6 |
| 1b6m | −14 | — | 0.2 | −12.7 | — | 3.2 |
| 1baf | −4.2 | — | 1.2 | −9.3 | — | 1 |
| 1bap | −8.9 | −9.4 | 0.3 | −11.6 | −9.4 | 0.4 |
| 1bbp | −15.2 | — | 5.1 | −13 | — | 5.1 |
| 1bkm | −11.1 | — | 3.6 | −15.4 | — | 2 |
| 1bma | −6.2 | — | 0.6 | −7.9 | — | 2.1 |
| 1bra | −5.4 | −2.5 | 2.3 | −7.2 | −2.5 | 0.3 |
| 1byb | −14.6 | — | 0.5 | −16.4 | — | 0.5 |
| 1c1b | −15.5 | — | 0.9 | −9.6 | — | 0.5 |
| 1c3i | −12.7 | — | 0.6 | −11.7 | — | 0.4 |
| 1c5p | −5.5 | — | 0.5 | −7.3 | — | 0.2 |
| 1c83 | −8.5 | — | 0.3 | −10 | — | 0.1 |
| 1c84 | −10.9 | — | 0.3 | −9.6 | — | 0.3 |
| 1c86 | −11.2 | — | 0.2 | −11.3 | — | 0.2 |
| 1c87 | −10.5 | — | 0.4 | −11.7 | — | 0.3 |
| 1c88 | −10.7 | — | 0.2 | −12.2 | — | 0.2 |
| 1c8k | −7.3 | — | 3.6 | −7.5 | — | 5.5 |
| 1cbs | −7.5 | — | 0.5 | −6.6 | — | 0.4 |
| 1cbx | −9.8 | −8.6 | 0.3 | −13.4 | −8.6 | 0.5 |
| 1cde | −15.1 | — | 2.3 | −10.6 | — | 2.1 |
| 1cdg | −5.6 | — | 6.9 | −5.7 | — | 6.5 |
| 1cil | −5.6 | — | 3.7 | −6.8 | — | 3.9 |
| 1cnx | −6.2 | — | 6.7 | −9.2 | — | 6.6 |
| 1com | −9.2 | — | 3.7 | −8.6 | — | 3.7 |
| 1coy | −8.8 | — | 0.4 | −8.7 | — | 0.3 |

| PDB entry | XP Score | ΔG_exp | XP RMS | SP Score | ΔG_exp | SP RMS | | PDB entry | XP Score | ΔG_exp | XP RMS | SP Score | ΔG_exp | SP RMS |
|---|---|---|---|---|---|---|---|---|---|---|---|---|---|---|
| 1ctr | −7.8 | −6.8 | 1 | −6.4 | −6.8 | 2.4 | | 1sre | −4.3 | −5.4 | 0.3 | −9.6 | −5.4 | 0.3 |
| 1ctt | −6.3 | −6.2 | 0.6 | −6.5 | −6.2 | 5 | | 1srj | −4.8 | — | 0.4 | −9.1 | — | 0.4 |
| 1d3d | −15.7 | — | 2.1 | −10.7 | — | 2.6 | | 1stp | −18.5 | −18.3 | 0.5 | −11.2 | −18.3 | 0.6 |
| 1d3p | −13.2 | — | 1.8 | −10.8 | — | 2.1 | | 1tdb | −8.1 | — | 7.4 | −6.9 | — | 7.5 |
| 1d7x | −7.2 | — | 0.5 | −9.7 | — | 0.4 | | 1thy | −5.2 | — | 2.3 | −7.4 | — | 2.5 |
| 1d8f | −7.7 | — | 9.3 | −9 | — | 4.8 | | 1tka | −11.2 | — | 1.7 | −15.2 | — | 2.3 |
| 1dbb | −13.2 | −12.3 | 0.3 | −9.4 | −12.3 | 0.4 | | 1tlp | −11.5 | −10.3 | 10.4 | −13.3 | −10.3 | 7.3 |
| 1dbj | −13.2 | −10.4 | 0.3 | −8.6 | −10.4 | 0.3 | | 1tmn | −10.2 | −10 | 2.9 | −12.7 | −10 | 2.8 |
| 1dbk | −12.7 | −11 | 0.9 | −8.1 | −11 | 0.4 | | 1tng | −6.5 | −4 | 0.2 | −7.3 | −4 | 0.2 |
| 1dbm | −12.6 | −12.9 | 0.5 | −9.1 | −12.9 | 2 | | 1tnh | −5.4 | −4.6 | 0.6 | −7.6 | −4.6 | 0.3 |
| 1dd6 | −14 | — | 8.1 | −11 | — | 8.1 | | 1tni | −3.6 | −2.3 | 2 | −5.9 | −2.3 | 2 |
| 1dds | −9.8 | −11.3 | 3.6 | −8.1 | −11.3 | 2.4 | | 1tnj | −4.1 | −2.7 | 0.5 | −6.5 | −2.7 | 0.4 |
| 1dhf | −9.5 | −10.1 | 5.8 | −9.3 | −10.1 | 5.6 | | 1tnk | −3.7 | −2 | 1.1 | −6.2 | −2 | 1 |
| 1did | −4.7 | — | 3.7 | −6.9 | — | 4.1 | | 1tnl | −4.1 | −2.6 | 0.4 | −6.2 | −2.6 | 0.2 |
| 1die | −5.9 | −2.9 | 0.4 | −7.7 | −2.9 | 0.8 | | 1tph | −5.2 | — | 0.2 | −8.2 | — | 0.2 |
| 1dih | −9.5 | −7.8 | 2.4 | −15.8 | −7.8 | 4 | | 1tpp | −7 | — | 0.3 | −7.7 | — | 1.1 |
| 1dm2 | −12.2 | — | 0.7 | −9.5 | — | 0.7 | | 1trk | −14.6 | — | 0.9 | −14.4 | — | 2.1 |
| 1dog | −7 | −5.5 | 3.7 | −10.3 | −5.5 | 3.7 | | 1tyl | −5.1 | — | 5.2 | −5.3 | — | 1.1 |
| 1drl | −4.7 | −5.57 | 0.3 | −7.8 | −5.57 | 1.5 | | 1ukz | −13.5 | — | 0.5 | −12.6 | — | 0.4 |
| 1dwb | −5.6 | −4 | 0.6 | −6.7 | −4 | 0.3 | | 1ulb | −6.4 | −7.2 | 0.3 | −9 | −7.2 | 0.4 |
| 1dwc | −10 | −10.3 | 2.1 | −10.5 | −10.3 | 0.8 | | 1wap | −8.1 | — | 0.2 | −9.9 | — | 0.2 |
| 1dwd | −13.7 | −11.4 | 1.4 | −11.5 | −11.4 | 1.4 | | 1xid | −6.3 | — | 4 | −6.4 | — | 4.3 |
| 1e5i | −9.9 | — | 0.3 | −10.8 | — | 0.2 | | 1xie | −5.3 | — | 2.6 | −6.7 | — | 3.9 |
| 1eap | −12.1 | — | 0.8 | −10.2 | — | 2.4 | | 2ack | −7.6 | — | 1.1 | −5.8 | — | 0.9 |
| 1ebg | −13 | −14.8 | 0.4 | −20 | −14.8 | 0.3 | | 2ada | −8.8 | — | 0.4 | −10.4 | — | 0.5 |
| 1ecv | −8.2 | — | 0.2 | −9.8 | — | 0.2 | | 2ak3 | −9.7 | −5.3 | 0.8 | −8.5 | −5.3 | 0.6 |
| 1eed | −10.2 | −6.7 | 11.6 | −10.7 | −6.7 | 10.8 | | 2cgr | −11 | −9.9 | 0.6 | −11.3 | −9.9 | 0.5 |
| 1ejn | −9.3 | — | 0.4 | −9.4 | — | 0.3 | | 2cht | −9.9 | — | 0.4 | −10.8 | — | 0.5 |
| 1ela | −8.1 | −8.7 | 2 | −5.7 | −8.7 | 10 | | 2cmd | −8.6 | — | 0.8 | −10 | — | 0.5 |
| 1elb | −2.2 | — | 4.1 | −7.6 | — | 5.2 | | 2cpp | −8.5 | −8.3 | 0.2 | −5.8 | −8.3 | 3 |
| 1elc | −7.3 | −9.8 | 7.5 | −6.3 | −9.8 | 7.8 | | 2ctc | −7.3 | −5.3 | 1.5 | −10.7 | −5.3 | 1.6 |
| 1eld | −8.5 | — | 0.8 | −4.7 | — | 6.7 | | 2dbl | −12.2 | −11.8 | 2 | −8.9 | −11.8 | 0.8 |
| 1ele | −8.1 | — | 0.4 | −6.8 | — | 0.3 | | 2gbp | −10.5 | −10.4 | 0.2 | −12.9 | −10.4 | 0.1 |
| 1epb | −9.7 | — | 2.6 | −6.5 | — | 2.3 | | 2ifb | −6.1 | −7.4 | 2.3 | −3.5 | −7.4 | 1.9 |
| 1eta | −3.8 | — | 1.2 | −4.1 | — | 1.7 | | 2lgs | −5.4 | — | 1 | −7.1 | — | 5.9 |
| 1etr | −11.5 | −10.1 | 0.7 | −9.5 | −10.1 | 0.7 | | 2mcp | −4 | −7.1 | 1.5 | −5.4 | −7.1 | 1.3 |
| 1ets | −13 | −11.6 | 1.3 | −11.8 | −11.6 | 1.4 | | 2phh | −10.1 | −6.4 | 0.4 | −8.6 | −6.4 | 0.4 |
| 1ett | −12.7 | −8.4 | 0.6 | −9.5 | −8.4 | 0.5 | | 2pk4 | −6.4 | −4.32 | 0.8 | −6.2 | −4.32 | 0.9 |
| 1ezq | −16.2 | — | 1 | −12.9 | — | 0.2 | | 2plv | −11.9 | — | 1.6 | −8.2 | — | 1.2 |
| 1f0r | −11 | — | 2.4 | −9.3 | — | 0.8 | | 2r04 | −7.4 | −6.22 | 1.1 | −7.4 | −6.22 | 0.7 |
| 1f0s | −11.1 | — | 1.7 | −8.5 | — | 0.3 | | 2r07 | −8.7 | — | 1.5 | −7.4 | — | 0.7 |
| 1f0t | −10.4 | — | 1.6 | −10 | — | 0.3 | | 2sim | −7.6 | — | 0.9 | −10.6 | — | 0.8 |
| 1f0u | −8.6 | — | 0.6 | −11.2 | — | 1.6 | | 2tmn | −11 | −6.7 | 0.6 | −12.1 | −6.7 | 0.6 |
| 1fen | −10.8 | — | 1.2 | −6.5 | — | 0.4 | | 2tpi | −8.7 | −5.9 | 0.4 | −8.1 | −5.9 | 1.2 |
| 1fh8 | −9.4 | — | 0.2 | −12.5 | — | 0.2 | | 2upj | −11.2 | −14.2 | 3.1 | −11.3 | −14.2 | 2.7 |
| 1fh9 | −7.8 | — | 0.8 | −8.4 | — | 6.5 | | 2xis | −6 | −7.9 | 2.3 | −8.1 | −7.9 | 2.4 |
| 1fhd | −9 | — | 5.4 | −11.3 | — | 0.4 | | 2yhx | −4.3 | — | 1.9 | −9.6 | — | 2.2 |
| 1fjs | −7.9 | — | 2 | −12.6 | — | 2.4 | | 3cla | −6.5 | −4.94 | 8.5 | −4.8 | −4.94 | 6.1 |
| 1fkg | −10.4 | — | 1.4 | −8.2 | — | 1.6 | | 3dfr | −13.8 | −14 | 0.7 | −13 | −14 | 0.8 |
| 1fki | −10.7 | — | 1.3 | −7.6 | — | 1.3 | | 3hvt | −8.8 | — | 0.7 | −8.1 | — | 0.8 |
| 1fq5 | −17.8 | — | 1.9 | −15.9 | — | 2.4 | | 3mth | −5.4 | — | 1.2 | −4.6 | — | 5.6 |
| 1fvt | −12.1 | — | 0.9 | −8.7 | — | 0.9 | | 3ptb | −6.1 | −6.5 | 0.3 | −7.4 | −6.5 | 0.2 |
| 1nco | −8 | — | 0.6 | −11.6 | — | 0.4 | | 3tpi | −7.3 | −5.9 | 0.6 | −9.4 | −5.9 | 0.5 |
| 1nis | −4.9 | — | 0.3 | −11.4 | — | 0.5 | | 4aah | −11.3 | — | 0.3 | −13.3 | — | 0.3 |
| 1nnb | −5.4 | −7.2 | 1.4 | −9.3 | −7.2 | 0.3 | | 4cts | −7.7 | — | 0.2 | −8.6 | — | 0.2 |
| 1nsc | −5.8 | −4.1 | 0.7 | −12 | −4.1 | 0.2 | | 4dfr | −12.7 | −13.2 | 1.1 | −12.1 | −13.2 | 1 |
| 1nsd | −7.2 | −7.2 | 1.1 | −10 | −7.2 | 0.3 | | 4fab | −16.4 | −14.4 | 4.5 | −8.8 | −14.4 | 0.8 |
| 1odw | −11 | — | 3.9 | −8.7 | — | 1.5 | | 4fbp | −11.7 | — | 2 | −13.9 | — | 0.5 |
| 1okl | −7.8 | — | 0.5 | −5.9 | — | 2.7 | | 4fxn | −11.2 | — | 0.7 | −16.6 | — | 1.2 |
| 1pbd | −11.3 | — | 0.3 | −9.4 | — | 0.3 | | 4hmg | −6.7 | −3.5 | 0.7 | −7 | −3.5 | 0.7 |
| 1pgp | −8.3 | −7.8 | 2.3 | −10.3 | −7.8 | 2.2 | | 4phv | −14.2 | −12.5 | 0.8 | −10.2 | −12.5 | 5.5 |
| 1pha | −12.5 | — | 0.7 | −8.6 | — | 0.5 | | 4tim | −0.8 | −2.16 | 0.8 | −11.3 | −2.16 | 1.3 |
| 1phd | −7.6 | — | 0.8 | −6.2 | — | 0.3 | | 4tln | −5.7 | −5.1 | 1.7 | −9.8 | −5.1 | 2.5 |
| 1phf | −7.9 | −6 | 1.8 | −5.3 | −6 | 1.1 | | 4tmn | −12.2 | −13.9 | 1.1 | −14.4 | −13.9 | 1.2 |
| 1phg | −11.2 | −11.8 | 1.7 | −7.7 | −11.8 | 1.2 | | 4tpi | −6.7 | −4 | 0.7 | −8.3 | −4 | 0.6 |
| 1poc | −10.7 | — | 2.5 | −12.4 | — | 1.5 | | 4tsl | −8.6 | −7.6 | 0.9 | −7.5 | −7.6 | 0.8 |
| 1ppc | −9.1 | −8.8 | 1.5 | −10.3 | −8.8 | 1.1 | | 5abp | −8.1 | −9 | 0.1 | −12.1 | −9 | 0.2 |
| 1pph | −8.6 | −8.5 | 0.9 | −9.9 | −8.5 | 0.6 | | 5cpp | −8.2 | −8 | 0.1 | −5.9 | −8 | 2.7 |
| 1ppi | −15.9 | — | 1 | −13.9 | — | 7.6 | | 5cts | −0.2 | — | 0.2 | −8.1 | — | 0.3 |
| 1ppk | −8.5 | −10.4 | 0.6 | −11.2 | −10.4 | 0.3 | | 5p2p | −9.6 | — | 1.9 | −9.2 | — | 10.4 |
| 1ppl | −9.7 | −11.5 | 0.9 | −12.2 | −11.5 | 2.6 | | 5tim | −1.5 | −3.1 | 0.9 | −7 | −3.1 | 0.7 |
| 1ppm | −9.3 | −7.9 | 0.5 | −12.9 | −7.9 | 0.6 | | 5tln | −11.6 | −8.7 | 2.4 | −12.1 | −8.7 | 1.8 |
| 1pro | −15.6 | −15.4 | 1.4 | −12.5 | −15.4 | 1.9 | | 5tmn | −10.9 | −11 | 2.6 | −13.3 | −11 | 2.8 |
| 1pso | −12.2 | −14.1 | 2.6 | −9.8 | −14.1 | 5.7 | | 6abp | −8.9 | −9.1 | 0.3 | −11.3 | −9.1 | 0.4 |
| 1sbg | −11.1 | −10.6 | 0.9 | −10.8 | −10.6 | 0.4 | | 6cpa | −11.4 | −15.7 | 4.8 | −14.9 | −15.7 | 4.2 |
| 1slt | −5.2 | — | 0.7 | −9.1 | — | 0.6 | | 6rnt | −5.5 | — | 0.6 | −8.2 | — | 0.6 |
| 1snc | −9.8 | −6.7 | 2.5 | −11.2 | −6.7 | 1.2 | | 6tim | −5.5 | −3.21 | 0.6 | −8.8 | −3.21 | 0.4 |

-continued

| PDB entry | XP Score | ΔG_exp | XP RMS | SP Score | ΔG_exp | SP RMS |
|---|---|---|---|---|---|---|
| 6tmn | −11.1 | −6.9 | 2.4 | −13.6 | −6.9 | 2.3 |
| 7abp | −6.2 | −8.1 | 0.2 | −11.7 | −8.1 | 0.2 |
| 7cpa | −15.9 | −19.1 | 3.9 | −15.2 | −19.1 | 4.1 |
| 7cpp | −6.3 | −5.2 | 2 | −4.6 | −5.2 | 3.2 |
| 7tim | −5.4 | — | 0.2 | −11 | — | 0.2 |
| 8abp | −7.9 | −10 | 0.2 | −12.4 | −10 | 0.2 |
| 8atc | −11.1 | — | 0.3 | −11.6 | — | 1.4 |
| 8gch | −7.1 | — | 0.5 | −9.6 | — | 0.3 |
| 9abp | −8 | −10.9 | 0.1 | −12.7 | −10.9 | 0.2 |
| 9hvp | −10.8 | −11.4 | 1.4 | −13.7 | −11.4 | 1.6 |
| 1g45 | −8.2 | — | 7.9 | −6.8 | — | 4.2 |
| 1g46 | −8.2 | — | 8.1 | −6.9 | — | 4.5 |
| 1g48 | −6.9 | — | 2 | −7.1 | — | 3.8 |
| 1g4j | −6.9 | — | 5.3 | −8 | — | 3.5 |
| 1g4o | −7.9 | — | 7.9 | −6.6 | — | 4.3 |
| 1g52 | −8.6 | — | 8 | −6.7 | — | 4.3 |
| 1g53 | −8.2 | — | 7.9 | −6.4 | — | 4.5 |
| 1g54 | −6.5 | — | 6 | −7.1 | — | 5.1 |
| 1ghb | −6.8 | — | 0.3 | −8.3 | — | 0.3 |
| 1glp | −4.2 | — | 0.8 | −10.8 | — | 0.3 |
| 1glq | −8.2 | — | 1.2 | −11.7 | — | 0.3 |
| 1gsp | −7.5 | — | 1 | −9.1 | — | 2.8 |
| 1hbv | −10.2 | −8.7 | 10.5* | −9.9 | −8.7 | 3.2 |
| 1hdc | −9.9 | — | 0.7 | −7.8 | — | 0.5 |
| 1hdy | −3.7 | — | 3.5 | −4 | — | 1.7 |
| 1hef | −10.1 | −12.1 | 6.1 | −11.4 | −12.1 | 6.8 |
| 1hfc | −9.2 | — | 2.4 | −10.3 | — | 2.3 |
| 1hgg | −6.8 | — | 1.5 | −8.7 | — | 1.4 |
| 1hgh | −6.2 | — | 0.6 | −5.7 | — | 2.3 |
| 1hgi | −6.4 | — | 0.6 | −7.7 | — | 0.2 |
| 1hgj | −4.8 | — | 0.3 | −6.4 | — | 0.4 |
| 1hih | −12.5 | −11.3 | 1.4 | −11.4 | −11.3 | 1.2 |
| 1hps | −12 | −12.6 | 12.1* | −12.8 | −12.6 | 12.1 |
| 1hpv | −9.8 | −12.6 | 0.9 | −10.3 | −12.6 | 0.9 |
| 1hpx | −12.1 | −11.2 | 2.1 | −12.1 | −11.2 | 3.5 |
| 1hri | −11.3 | — | 10.5* | −6 | — | 3.9 |
| 1hsg | −14.3 | −12.8 | 3.8 | −13.7 | −12.8 | 0.4 |
| 1hsl | −9.8 | −7.3 | 1.3 | −9.8 | −7.3 | 1.3 |
| 1hte | −10.1 | −8.6 | 7.3* | −8.7 | −8.6 | 1.2 |
| 1htf | −11.2 | −11.1 | 3.3 | −10.1 | −11.1 | 2.2 |
| 1hti | −4.3 | — | 4.4 | −6 | — | 1.7 |
| 1hvr | −13.4 | −13 | 1.6 | −5.2 | −13 | 3.9 |
| 1hyt | −8.8 | — | 2.6 | −10.5 | — | 0.9 |
| 1icn | −7.4 | — | 9.3 | −1 | — | 8.9 |
| 1ida | −9.9 | — | 2 | −12.6 | — | 12.1 |
| 1igj | −6.8 | — | 0.7 | −7.5 | — | 0.5 |
| 1imb | −6.8 | — | 1.8 | −11 | — | 1.6 |
| 1ivb | −6.2 | — | 0.5 | −6.8 | — | 0.5 |
| 1ivc | −5.1 | — | 1.8 | −6.4 | — | 1.9 |
| 1ivd | −3.5 | — | 0.8 | −6.8 | — | 0.7 |
| 1ive | −6.1 | — | 4.8 | −6.4 | — | 5 |
| 1ivf | −8.2 | — | 0.7 | −8.3 | — | 1.3 |
| 1lah | −5.9 | — | 0.2 | −10.7 | — | 0.1 |
| 1lcp | −8.3 | — | 1.8 | −8.9 | — | 1 |
| 1ldm | −7.4 | −7.4 | 1.3 | −6.4 | −7.4 | 1.3 |
| 1lic | −4.8 | — | 4.8 | −2.8 | — | 2.4 |
| 1lmo | −6.8 | — | 7.1 | −8 | — | 0.9 |
| 1lna | −6.4 | — | 1.3 | −8.2 | — | 0.7 |
| 1lst | −6.3 | — | 0.7 | −8.6 | — | 0.3 |
| 1mbi | −3.9 | −2.6 | 1.9 | −3.5 | −2.6 | 1.6 |
| 1mcr | −10.1 | — | 6 | −7.6 | — | 1.7 |
| 1mdr | −8.5 | — | 1.7 | −9.2 | — | 0.5 |
| 1mfe | −8.8 | −7.2 | 6.2* | −8.4 | −7.2 | 1.8 |
| 1mld | −8.5 | — | 0.3 | −10.2 | — | 0.2 |
| 1mmq | −9.7 | — | 0.6 | −11.4 | — | 0.3 |
| 1mnc | −9.8 | −12.3 | 0.3 | −11.4 | −12.3 | 0.4 |
| 1mrg | −6.2 | — | 0.2 | −7.5 | — | 0.1 |
| 1mrk | −13.3 | — | 1.2 | −10 | — | 1.2 |
| 1mup | −5.2 | — | 4.9 | −4.9 | — | 4.1 |

The average RMSD of the XP score calculated from the experimental binding affinities using our scoring function is 1.8 kcal/mole, which represents a roughly two fold improvement over the SP scoring RMSD of 3.3 kcal/mole for the same data set. We note that the RMSD calculation discussed above incorporates estimates of receptor strain energy, which leads to a small modification of the errors that would be computed from the table above for a few cases. There are very few cases using our scoring function with errors greater than 3 kcal/mole, which implies that the present scoring function has an excellent ability to distinguish weak (millimolar), moderate (micromolar), and strong (nanomolar) binders from each other, a principal task in virtual screening, a capability that is only marginally present in prior scoring functions. To improve beyond this level with regard to precision, we believe that receptor flexibility must be introduced, and an additional level of detail with regard to the protein-ligand interactions must be incorporated.

Efficacy of our method is also based on docking a set of known active compounds for a particular receptor into that receptor, and in addition docking a database of 1,000 randomly chosen drug-like molecules as a comparison set. We calculate the "enrichment" of active compounds by our new scoring function (defined below) as compared to the database ligands, and compare the results with several older, less effective scoring functions.

Our test set includes only ligands that fit into the particular version of the receptor under study. Forms of the receptor are chosen that are relatively "open" to maximize the number of ligands that fit. We report the fraction of fitting ligands that we have retained from an initial data set that we investigated. Ligands have been discarded primarily on the basis of steric clashes blocking access to a pocket. Any ligand achieving a reasonable binding mode (assessed either via direct comparison with an experimental structure, or by analogy with a known structure) has been retained regardless of the score it is assigned.

Only ligands that have experimental binding affinities of better than 10 μM are used in calculating the enrichment score. The binding affinities of some ligands that bind less strongly than this are calculated as a check on the ability of our scoring function to discriminate weakly- and strongly-binding ligands. The 10 μM cutoff is chosen because this is what is typically used to define "active" compounds in high throughput screening experiments. The percent of random database ligands expected to compete at this range of activity (assuming perfect computational and experimental assessment of binding affinity) is typically on the order of 0.1-1.0% (although these numbers can be significantly higher or lower depending upon the receptor) or 1-10 compounds in a database of 1,000 randomly chosen compounds. True positives in the random database thus would be expected to introduce relatively little noise into our enrichment data. The following table illustrates total actives with 10 μM or better binding affinity compared to the total that fit and dock into the chosen receptor of each screen.

| Screen | Total actives | Total docked well |
|---|---|---|
| Thrombin | 15 | 15 |
| HIV-RT | 32 | 24 |
| COX-2 | 19 | 17 |
| P38 1kv2 | 10 | 10 |
| P38 bl7 | 50 | 37 |
| EGFR-tk | 127 | 110 |
| CDK-2 | 10 | 6 |
| TK | 7 | 6 |
| Fxa | 20 | 16 |
| Estrogen | 10 | 8 |
| LCK | 169 | 121 |
| Neuramid. | 9 | 9 |
| AchE | 28 | 25 |
| HIV-protease | 15 | 14 |

Standard definitions of enrichment encounter problems when a large number of ligands are used in a test set relative to the size of the random database. We use a definition that is independent of the number of actives in the test set, as it is determined solely by the number of random database ligands that score better than each active (thus, the rank of the actives relative to each other is eliminated as an element).

The following table presents the average number of database ligands outranking the set of known active compounds for the receptors we have studied, for three different scoring functions; the new scoring function, containing the terms enabled by our methods described above; and two older scoring functions, which are known to be competitive with other approaches in the literature. Actives have at least 10 uM activity. The requisite average is computed by determining the number of database ligands which outrank each active, then adding together these values and dividing by the number of actives. Thus, a value of zero entered in the table below represents a perfect score, in which all of the actives outrank all of the database ligands. It can be seen that, by this measure, the current scoring function is qualitatively better than the old scoring functions for many (if not most receptors) often by a factor of 10 or more.

| Screen | Average Outranking Decoys | | |
| --- | --- | --- | --- |
| | Current Scoring Scoring Function | Old 1 Scoring Function | Old 2 Scoring Function |
| AchE | 80 | 560 | 389 |
| Neuramididase | 14 | 523 | 113 |
| Factor XA | 5 | 179 | 46 |
| P38 1kv2 | 1 | 25 | 187 |
| P38 1bl7 | 16 | 133 | 278 |
| HIV-RT | 15 | 46 | 110 |
| COX-2 | 18 | 57 | 121 |
| CDK-2 | 2 | 18 | 180 |
| Thrombin | 1 | 76 | 17 |
| HIV protease | 22 | 124 | 60 |
| Estrogen | 11 | 4 | 25 |
| LCK kinase | 35 | 317 | 291 |
| EGFR | 32 | 407 | 452 |
| Thermolysin | 5 | N/A | 0 |
| Thymidine Kinase | 0 | 0 | 13 |

The methods described above can be used in many ways. In one particular example, as described, the methods can be used to calculate numerical values for contributions of various terms to the binding affinity. In another particular example, the key contributors to each term can be visually illustrated in a graphical user interface (GUI). Visualization of such terms is useful in the design of new molecules, which would better exploit the key features of the protein active site cavity (such as sites where waters are hydrophobically enclosed as previously described). A visualization can also be used to ascertain regions of an active compound that are unimportant to achieving tight binding to the protein. Such regions can then be modified by medicinal chemists to give the molecule other properties that are necessary for pharmaceutical effectiveness in vivo, for example, better absorption through the digestive system, avoidance of toxicity, increased solubility, and amelioration of unfavorable metabolic reactions.

Hydrophobic enclosure can be visualized by identifying the group of hydrophobic atoms in the ligand which are enclosed, identifying the protein atoms or residues which are detected by the algorithm to participate in the enclosure, and using shape, color, and texture of the display of the relevant ligand and protein atoms to highlight these regions.

This visualization can enable a medicinal chemist to understand which parts of the ligand must remain hydrophobic (i.e., should not be modified to incorporate a hydrophilic group), and which residues/atoms of the protein are responsible for creating the enclosure. It is also possible to use data from multiple ligands to create a complete map of regions of the protein that are capable of leading to a favorable enclosure term. One can then design a new ligand that exploits as many of these regions as possible, and exploits each region to the fullest extent.

Special neutral-neutral hydrogen bonds that get rewards can be visualized by highlighting the protein and the ligand donor and acceptor groups that form the hydrogen bonds in question, as well as the protein groups contributing to the required hydrophobic enclosure of the hydrogen bond. Such visualization would indicate key groups on the ligand that should only be replaced by other groups capable of achieving the same special rewards.

Special charged-charged hydrogen bonds can be visualized by highlighting the protein and ligand donor and acceptor groups that form the hydrogen bond(s) in question.

For both neutral-neutral and charged-charged hydrogen bonds, there is a criterion for assigning the reward that involves assessing the degree of solvation of the relevant group in the protein. This can be visualized by displaying explicit waters surrounding the relevant groups.

Visualization can be useful even if the numerical contributions to binding affinity are not calculated. Visualization can make a specific contribution to the design of novel compounds, and lead to optimization processes in which active compounds are modified to improve a wide range of properties while retaining potency.

Embodiments of the invention can be implemented in digital electronic circuitry (or in computer hardware, firmware, software), or in combinations of them. Embodiments of the invention can be implemented as a computer program product, i.e., a computer program tangibly embodied in an information carrier (e.g., in a machine readable storage device or in a propagated signal) for execution by, or to control the operation of, data processing apparatus (e.g., a programmable processor, a computer, or multiple computers). A computer program can be written in any form of programming language, including compiled or interpreted languages, and it can be deployed in any form, including as a stand alone program or as a module, component, subroutine, or other unit suitable for use in a computing environment. A computer program can be deployed to be executed on one computer or on multiple computers at one site or distributed across multiple sites and interconnected by a communication network.

Method steps of embodiments of the invention can be performed by one or more programmable processors executing a computer program to perform functions of the invention by operating on input data and generating output. Method steps can also be performed by, and apparatus of the invention can be implemented as, special purpose logic circuitry (e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks). Information carriers suitable for embodying computer program instructions and data include all forms of non volatile memory, including by way of example semiconductor memory devices (e.g., EPROM, EEPROM, and flash memory devices; magnetic disks (e.g., internal hard disks or removable disks; magneto optical disks; and CD ROM and DVD-ROM disks). The processor and the memory can be supplemented by, or incorporated in special purpose logic circuitry.

The invention can be implemented in a computing system that includes a back end component (e.g., as a data server) or that includes a middleware component (e.g., an application server) or that includes a front end component (e.g., a client computer having a graphical user interface or a Web browser through which a user can interact with an implementation of the invention) or any combination of such back end, middleware, or front end components. The components of the system can be interconnected by any form or medium of digital data communication (e.g., a communication network). Examples of communication networks include a local area network ("LAN") and a wide area network ("WAN") (e.g., the Internet).

The computing system can include clients and servers. A client and server are generally remote from each other and typically interact through a communication network. The relationship of client and server arises by virtue of computer programs running on the respective computers and having a client-server relationship to each other.

It is to be understood that the foregoing description is intended to illustrate and not to limit the scope of the invention, which is defined by the scope of the appended claims.

APPENDIX I

Hydrophobic Packing Scoring

1) Assign Ligand Hydrophobic Groups:

Ligand atoms are assigned to $N_g$ 'phobic groups' each with a set of atoms $\{j\}$. Each phobic group is defined by a set of connected carbon atoms, uninterrupted by polar atom connections. Carbon atoms connected to polar atoms are not included in the group. Groups of size one do not contribute to the scoring.

From this point on the scoring is done for each group with the net score being the sum of the scores for each group. The following (steps 2 through 6) describes the scoring for any particular group.

2) Calculate Contacts with Phobic Protein Atoms;

For each ligand atom j that is in the phobic group, calculate the total number of contacts, cont(j) with phobic protein atoms that are within a distance of 3.0 A plus the sum of the vdw radii of the ligand (vdw_j) and the protein atom (vdw_k) (the total sum is approximately out 6 A for typical ligand and protein atoms). For each contact pair $c_{jk}$ corresponding to atom pairs (j,k), store the contact distance $r\_(j,c_{jk})$ and the vector $v(j,c_{jk})=r_k-r_j$ between the contacting ligand and protein atoms. As stated above r_jk<=3.0+vdw_i+vdw_j. In this process keep track of the contact pair jk_min with the smallest contact distance r_jk. Label the vector of the smallest contact pair $v_0$ This vector is referred to as the 'reference vector'.

3) Calculate Angles with Reference Vector.

For each ligand atom j in the group and all of its contacts $c_{jk}=(1, cont(j))$, calculate the angle, $ang(j,c_{jk})$ between the vector $v(j,c_{jk})$ and the reference vector $v_0$ 4) Calculate Radial Contact Score.

For a given atom j of a group, the radial contact score $S_j(r)$ is a linear ramp function between 0 and 1 derived as follows from the total contacts the ligand makes, cont(j).

$$S_j(r)=0.0 \text{ if cont}(j)<=20$$

$$S_j(r)=1.0 \text{ if cont}(j)>=32$$

$$S_j(r)=(\text{cont}(j)-20.0)/12.0 \text{ if } 20<\text{cont}(j)<32. \quad (A1)$$

5) Calculate Angular Score.

For a given atom j of the group and each contact $c_{jk}(c_{jk}=1, cont(j))$ that atoms makes, an angular score, $S_{jk}(a)$ is calculated. To calculate this score it is first necessary to bin the contact distance $r\_(j,c_{jk})$ into an integer values m=1-6 by simple integer truncation of the real valued distance. The angular score is then a linear ramp function of the angle $ang(j,c_{jk})$ with boundaries determined by the contact bin m;

$$S_{jk}(a)=0.0 \text{ if } ang(j,c_{jk})<amin(m)$$

$$S_{jk}(a)=1.0 \text{ if } ang(j,c_{jk})>amax(m)$$

$$S_{jk}(a)=wt(m)*(ang(j,c_{jk})-amin(m))/(amax(m)-amin(m)). \quad (A2)$$

with amax(m) and amin(m) being maximum and minimum angles per bin m as follows (in degrees)

m=1-3: amin=120, amax=140
m=4 amin=120, amax=140
m=5 amin=140, amax=180
m=6 amin=150, amax=180 and wt(m) is weight factor for each angular range:

m=1-4; wt=1.0
m=5 wt=0.7
m=6 wt=0.6

The total angular score Sj(a) for atom j is then calculated as simply the sum of all Sjk(a);

$$S_j(a)=\Sigma_{k=1,cont(j)}S_{jk}(a) \quad (A4)$$

6) Calculate Total Group Score, Total Packing Score.

The total group packing score for the ith group $S_g(i)$ is simply the sum of the angular scores $S_j(a)$ multiplied by the contact scores $S_j(r)$;

$$S_g(i)=\Sigma_j S_j(r)*S_j(a). \quad (A5)$$

The total hydrophobic packing score $E_{pho\_pack}$ is the negative sum of the group scores;

$$E_{pho\_pack}=\Sigma_{i=1,Ng}S_g(i). \quad (A6)$$

APPENDIX II

Scaling of Special H Bond Rewards

The following describes the scaling of the special H bond score ($E_{HB\_spec}$) as the geometry differs from ideality.

A typical H-bond between is between a hydrogen 'donor' (NH bond for example), and a 'hydrogen acceptor' (O atom of carbonyl). The quality of the H bond is measured by the extent to which the angle θ between the N-H bond vector and the H—O vector differs from colinearity (a 180 degree angle is colinear). In addition the distance ROH between the H and O atoms is ideally in the range of approximately 1.8 A. The typical H bond scoring function uses linear functions of the parameters θ and $R_{OH}$ to assign a quality of the H bond $E_{hb}$ as;

$$E_{hb}=A*S(r)*S(\theta) \quad (A9)$$

where A is a constant and S(r) measures deviation from the 'optimal' distance $r_0$;

$$S(r)=1.0, \text{ if } R_{OH}\leq r_0$$

$$S(r)=(R_{OH}-r_0)/(r_m-r_0), \text{ if } r_0<R_{OH}<r_m$$

$$S(r)=0.0, \text{ if } R_{OH}\geq r_m \quad (A10)$$

$r_m$ is the maximum allowable H bond distance. The angular function has a similar form:

$$S(\theta)=1.0, \text{ if } \theta\geq\theta\_o$$

$$S(\theta)=(\theta-\theta_m)/(\theta_0-\theta_m), \text{ if } \theta_m<\theta<\theta_0$$

$$S(\theta)=0.0, \text{ if } \theta<\theta_m \quad (A11)$$

where $\theta_0$ is the maximal angle and $\theta_m$ is the minimal angle allowed in the parametrization.

For an H bond to qualify as one of a special H bond pair, it must have an $E_{hb}$ value above −0.05 as parameterized in Glide. Once the special H bond is additionally declared as meeting all of the criteria described in Sec. C, a base reward $E_{base}$ of −3 or −2 is assigned (−3 for one pair and −2 for the second pair if two pairs which share the same atom exist). This base reward is then scaled down using an angular function of the form of Eq. (A11) with $\theta_0$ as 135° and $\theta_m$ of 120°. Each bond of the pair is assigned an angular scale factor S1, S2. The product of the angular scale factor for each bond S1*S2 of the pair is the net scale factor applied to the base reward, $$E_{hb\_spec} = S1 * S2 * E_{base} \quad (A12)$$

If the ligand atom is formally charged, no scale factor is applied.

A second class of H bonds involves acceptor atoms in rings (typically N atoms) with an H atom. In this case the quality of the H bond is optimal when the donor axis is parallel to the ring donor lone pair direction. The lone pair direction is approximated as the sum of the vectors connect the atoms R1 to A, and R2 to A, where R1 and R2 are the ring atoms connected to the ring acceptor atom A. The angle $\theta$ between the lone pair vector and the N-H donor axis is calculated. A scale factor $S_{lp}$ of the form of Eq. (A11) is calculated with $\theta_0 = 130°$ and $\theta_m = 100°$. In these cases the scale factors S1 or S2 are multiplied by $S_{lp}$, that is two angular functions scale a given H bond scale of the pair.

Other embodiments are within the scope of the following claims.

What is claimed is:

1. A computer-implemented method for characterizing interaction of a proposed ligand with a specified receptor by accessing data from which the computer calculates a value representative of said interaction (VRI), said method comprising computer-scoring of hydrophobic interactions between one or more ligand atoms and one or more receptor atoms, said computer scoring comprising at least the following steps:
   a) the computer(s) receiving data from the database representative of atoms in the ligand docked with the receptor;
   b) the computer(s) acting on said data to identify groups of at least three covalently connected lipophilic ligand atoms that exhibit hydrophobic interaction with one or more lipophilic receptor atoms and scoring hydrophobic interactions of said ligand atoms with said receptor atoms;
   c) the computer(s) assigning a bonus for the presence of hydrophobic enclosure for each said group of at least three covalently connected lipophilic ligand atoms exhibiting hydrophobic interaction with receptor atoms on two sides of said group, and not for any group whose size is below three; and
   d) the computer(s) calculating the VRI including said bonus determined in step (c).

2. The method of claim 1 in which calculation of VRI further includes at least one term representative of at least one of the following: free energy, enthalpy, and entropy.

3. The method of claim 1 in which scoring hydrophobic interactions includes calculating a surface area scoring component (SASC) that varies as a function of the surface area of hydrophobic-hydrophobic contact between ligand atoms and receptor atoms, and the bonus for the presence of hydrophobic enclosure results in an increase in VRI relative to a hypothetical VRI that would be obtained using the SASC but not the bonus.

4. The method of claim 1 in which scoring hydrophobic interactions includes calculating an atom-atom pair energy term, and the bonus for the presence of hydrophobic enclosure results in an increase in VRI relative to a hypothetical VRI that would be obtained using the sum of atom-atom pair energy term but not the bonus.

5. The method of claim 3 in which scoring hydrophobic interactions further includes calculating an atom-atom pair energy term, and the bonus for the presence of hydrophobic enclosure results in an increase in VRI relative to a hypothetical VRI that would be obtained using the sum of atom-atom pair energy terms plus the SASC term, but not the bonus.

6. The method of any of claims 1-5 wherein said VRI value is used by a computer program and the method is used to simulate docking of the ligand into the receptor to produce the structure of the receptor-ligand complex.

7. The method of claim 6 wherein the method is used to assist in assigning a structure to the receptor-ligand complex.

8. The method of claim 6 wherein the VRI is used to assess binding affinity of the ligand to a protein-ligand complex structure produced by the docking program.

9. The method of any of claims 1, 2 or 4 wherein calculating said VRI value comprises assigning a value representative of receptor-ligand interaction in a pre-determined receptor-ligand structure.

10. The method of claim 9 wherein said pre-determined receptor-ligand structure is obtained from a docking program from molecular dynamics simulations, or from minimizations using a continuum solvation model.

11. The method of any of claims 1, 2 or 4 further comprising generating a graphical display of structural features of the receptor-ligand complex that contribute to enhanced VRI due to hydrophobic enclosure.

12. The method of claim 11 further comprising producing a computer-generated graphical display of the complex in which receptor atoms contributing to the hydrophobic enclosure of one or more ligand atoms are graphically highlighted provide a physical picture of the enclosure.

13. The method of claim 11 in which surfaces of the receptor that are involved in hydrophobic enclosure of the ligand are highlighted in the display.

14. The method of any of claims 1-4 wherein said method is used to select compounds to be tested experimentally.

15. The method of claim 1 in which the method comprises one or more of the following steps in any order (so long as step (g) is performed last):
   a) calculating a term representing said hydrophobic enclosure bonus;
   b) calculating a term representing electrostatic rewards;
   c) calculating a term enhancing VRI for hydrogen (H) bonds in hydrophobic regions;
   d) calculating a term representing H bond pairs;
   e) calculating terms representing π-cation and π stacking;
   f) calculating a term representing a standard lipophilic pair; and
   g) calculating the score from a sum of terms.

16. The method of claim 1 in which the presence of hydrophobic enclosure is determined by performing at least the following steps:
   a) locating lipophilic receptor atoms that are within a specified cut-off distance of a hydrophobic atom of the ligand;
   b) determining the spatial and angular distribution of lipophilic receptor atoms around the hydrophobic ligand atom;

c) awarding the bonus based on the spatial and angular distribution of the lipophilic receptor atoms around the hydrophobic ligand atom.

17. The method of claim 1 which a value for the bonus attributable to said connected group of ligand atoms is determined by performing at least the following steps:
   a) the computer(s) calculating the distance between a lipophilic ligand atom in the group and one or more lipophilic atoms of the receptor;
   b) the computer(s) assessing the degree of enclosure of the lipophilic ligand atom by a formula which includes terms representing the angular dispersion of the lipophilic receptor atoms and their distance from the lipophilic ligand atom, and assigning the value for the bonus being based on said assessment of the degree of enclosure.

18. The method of claim 17 in which greater angular dispersion of receptor atoms that are within a specified cut-off distance of the ligand atom results in a higher VRI using said formula.

19. The method of claim 1 in which said group of connected ligand atoms includes a set of connected carbon atoms uninterrupted by polar atom connections.

20. The method of claim 1 in which the ligand includes groups of neutral ligand atoms and the method includes:
   a) identifying one or more hydrogen bonds between the neutral ligand atoms and the receptor;
   b) determining atoms of the ligand connected to the hydrogen bonding group or groups;
   c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, said method being further characterized in that a single hydrogen bond of the ligand with the receptor is detected, and a special single hydrogen bond bonus is awarded if that hydrogen bond and its environment satisfy one or more of the following conditions:
   (a) a hydrogen bond donor or acceptor atom of the ligand is: i) nitrogen; ii) in a ring or iii) both (i) and (ii);
   (b) a ligand atom forms part of a group of hydrogen bond donor atoms and all donors of the group are hydrogen bonded to the receptor;
   (c) the receptor is a protein and receptor atoms participating in the hydrogen bond are part of the protein backbone;
   (d) the relevant receptor donor or acceptor atom in the apoprotein structure is poorly solvated;
   (e) the sum of the angular factors in the enclosure terms for the ligand heavy atom involved in the hydrogen bond and any carbon atoms attached to this atom is calculated, and the sum is required to exceed a specified threshold and
   a special single hydrogen bond bonus is awarded if that hydrogen bond and its environment satisfy the following condition: the sum of the angular factors in the enclosure terms for the ligand heavy atom involved in the hydrogen bond and any carbon atoms attached to this atom is calculated, and the sum is required to exceed a specified threshold.

21. The method of claim 1 in which the ligand includes groups of neutral ligand atoms and the method includes:
   a) identifying one or more hydrogen bonds between the neutral ligand atoms and the receptor;
   b) determining atoms of the ligand connected to the hydrogen bonding group or groups;
   c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, further characterized in that in which step (d) comprises using a grid based water addition program to assess the solvation of the donor or acceptor atom in an apoprotein structure of the receptor.

22. The method of claim 21 in which atoms are required to have fewer than 3 waters in contact in order to qualify for the special hydrogen bond bonus.

23. The method of claim 1 in which the ligand includes groups of neutral ligand atoms and the scoring of hydrophobic interactions includes:
   a) identifying one or more hydrogen bonds between the neutral ligand atoms and the receptor;
   b) determining atoms of the ligand connected to the hydrogen bonding group or groups;
   c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, the method comprising designating pairs of ligand-receptor hydrogen bonds and awarding a special pair hydrogen bond bonus using one or more of the following criteria:
   (i) pairs of multiple hydrogen bonds do not qualify for the special pair hydrogen bond bonus when the bonding atoms are separated by more than one rotatable bond, where OH groups count as non-rotatable in this calculation;
   (ii) one or more of the following types of pairs of ligand receptor hydrogen bonds do not qualify for the special pair hydrogen bond bonus:

---

1) poor quality H bonds (<0.05 HB pair score.);
2) pairs involving the same neutral protein atom;
3) pairs involved in a salt bridge if the electrostatic potential at either ligand atom is not below a cutoff;
4) salt bridge pairs if either receptor atom is involved in a protein—protein salt bridge;
5) ligand donor/donor pairs which come from $NH_x$ $x >= 2$ groups where N is not part of a ring and has zero formal charge;
6) formally charged protein atoms with more than 8 second shell waters in the unligated state;
7) charged-neutral H bonds where the protein atom is not in a salt bridge;
8) pairs of different neutral acceptor atoms on the ligand;
9) Neutral H bond pairs that do not individually qualify for single hydrogen bond rewards; and
10) ligand OH to receptor H bonds if the receptor atom has zero formal charge

---

(iii) for pairs in which the ligand atoms of the pair individually have zero net formal charge, the hydrogen bonds are awarded a bonus for said hydrophobic enclosure where scoring said hydrophobic interaction is optimized for hydrogen bond pairs.

24. The method of claim 22, in which the following conditions are used in performing step (c) of claim 22 to determine whether the hydrogen bond pair has a hydrophobic enclosure score above a cut-off score so as to receive the hydrogen bond pair bonus:
  a) ligand atoms in the pair must be part of the same ring or, for non-ring ligand atoms, the ligand atoms must be directly connected to the same ring; and
  b) hydrophobicity of a hydrogen bond region is detected and angular factors for enclosure terms are added and the sum exceeds said specified threshold using the pair of hydrogen bonding ligand atoms and the ligand ring atoms directly connected to the ligand atoms participating in the hydrogen bond; and
  c) if a ligand atom of the pair is not a ring atom but is connected to a ring, the sum includes atoms of the ring which are next neighbors to the non-ring ligand atom.

25. The method of claim 23 in which double counting of pair and single special hydrogen bonds is avoided by looking for pairs first and excluding any rewarded hydrogen bonds found in the pair list from the single H bond reward list.

26. The method of claim 23 in which each of the following criteria is applied:
  d) ligand atoms in the pair must be part of the same ring or, for non-ring ligand atoms, the ligand atoms must be directly connected to the same ring;
  e) hydrophobicity of a hydrogen bond region is detected and angular factors for enclosure terms are added as described in claim 31, part (e), using the pair of hydrogen bonding ligand atoms and the ligand ring atoms directly connected to the ligand atoms participating in the hydrogen bond;
  f) if a ligand atom of the pair is not a ring atom but is connected to a ring, the sum includes atoms of the ring which are next neighbors to the non-ring ligand atom; and
  g) the bonus awarded to the hydrogen bond pair is −3 kcal/mole.

27. The method of claim 1 in which the ligand includes groups of neutral ligand atoms and the scoring of hydrophobic interactions includes:
  a) identifying one or more hydrogen bonds between the neutral ligand atoms and the receptor;
  b) determining atoms of the ligand connected to the hydrogen bonding group or groups;
  c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, and in which the magnitude of the bonus for hydrophobic enclosure is evaluated by at least the following steps:
  determining the presence of singlet hydrogen bonds, correlated pairs of hydrogen bonds and triplets of hydrogen bonds, and
  assigning different per-bond values to singlet, pair, and triplets of hydrogen bonds.

28. The method according to claim 1 in which the ligand includes groups of neutral ligand atoms and the scoring of hydrophobic interactions includes:
  a) identifying one or more hydrogen bonds between the neutral ligand atoms and the receptor;
  b) determining atoms of the ligand connected to the hydrogen bonding group or groups;
  c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, and in which
  the method which assigns a value for hydrogen bonds between groups of neutral atoms of a ligand and a receptor by a method comprising,
  assessing the degree of solvation of the receptor, and
  awarding a neutral-neutral hydrogen bond reward depending on the degree of receptor solvation.

29. The method of claim 1 in which the ligand includes groups of neutral ligand atoms and the scoring of hydrophobic interactions includes:
  a) identifying one or more hydrogen bonds between the neutral ligand atoms and the receptor;
  b) determining atoms of the ligand connected to the hydrogen bonding group or groups;
  c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, and in which
  two pairs of hydrogen bonds satisfy the criteria for awarding a bonus, and the two pairs share an atom in common.

30. The method of claim 29 in which the bonus for the second pair is −2 kcal/mole.

31. The method of claim 23 in which the bonus assigned to the pair of hydrogen bonds (referred to below as the "base reward") is reduced according to the following formulation:
  scaling the base reward down using an angular function:

$$S(\theta)=(\theta-\theta_m)/(\theta_0-\theta_m), \text{ if } \theta_m<\theta<\theta_0$$

where $\theta_0$ is the maximal angle and $\theta_m$ is the minimal angle allowed in the parametrization, $S(\theta)=1.0$, if $\theta \geq \theta_0$ and $S(\theta)= 0.0$, if $\theta<\theta_m$
  assigning each bond of the pair an angular scale factor S1, S2; and
  applying the product ($E_{hb\_spec}$) of the angular scale factor for each bond S1*S2 of the pair to the base reward ($E_{base}$), according to the formula $E_{hb\_spec}=S1*S2*E_{base}$.

32. The method of claim 31 in which $\theta_0$ is 135°±5° and $\theta_m$ is 120°±5°.

33. The method of claim 28 in which solvation of hydrogen bonding partners of the protein in a neutral-neutral hydrogen bond is evaluated by applying a grid-based algorithm for adding explicit waters, and counting the number of such waters in the first and second shell around the protein group in question.

34. The method of claim 1 in which the ligand includes groups of neutral ligand atoms and the scoring of hydrophobic interactions includes:
  a) identifying one or more hydrogen bonds between the neutral ligand atoms and the receptor;
  b) determining atoms of the ligand connected to the hydrogen bonding group or groups;
  c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, and in which the method further comprises producing a computer-generated depiction of the complex in which hydrogen bonds receiving a special bonus due to hydrophobic enclosure are highlighted in a graphical display.

35. The method of claim 1 in which the ligand includes groups of neutral ligand atoms and the method includes:
   a) identifying one or more hydrogen bonds between the neutral ligand atoms and the receptor;
   b) determining atoms of the ligand connected to the hydrogen bonding group or groups;
   c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, and
   the enclosure of hydrogen bonds receiving a special bonus due to hydrophobic enclosure is highlighted in a computer-generated graphical display.

36. The method of claim 35 in which receptor atoms participating in the hydrophobic enclosure of hydrogen bonds receiving a bonus are highlighted in a graphical display.

37. The method of claim 35 in which receptor atoms participating in the hydrophobic enclosure of hydrogen bonds receiving a bonus are highlighted via a display of hydrophobic surfaces of the receptor.

38. The method of claim 1 in which the ligand includes groups of neutral ligand atoms and the scoring of hydrophobic interactions includes:
   a) identifying one or more hydrogen bonds between the neutral ligand atoms and the receptor;
   b) determining atoms of the ligand connected to the hydrogen bonding group or groups;
   c) assigning a bonus to hydrogen bonds based on (a) whether there is hydrophobic enclosure of the ligand atoms involved in the hydrogen bonds, and the ligand atoms connected to the hydrogen bonding groups, and also on (b) whether the ligand atoms identified in (a) benefit from enclosure in that (i) the ligand atoms are lipophilic or (ii) the ligand atoms have made their full complement of hydrogen bonds without the enclosure, and in which the method further comprises producing a computer-generated depiction of the complex in which ligand atoms connected to hydrogen bonds receiving a special bonus due to hydrophobic enclosure are highlighted in a graphical display.

39. The method of claim 1 in which regions of the receptor capable of providing hydrophobic enclosure to suitable ligand groups are detected by carrying out molecular dynamics simulations, and identifying regions where the water molecules have unfavorable chemical potentials.

40. The method of claim 1 or in which regions of the receptor capable of providing hydrophobic enclosure to suitable ligand groups are detected by placing water molecules surrounding the receptor and detecting enclosed environments of these water molecules.

* * * * *

UNITED STATES PATENT AND TRADEMARK OFFICE
CERTIFICATE OF CORRECTION

| | |
|---|---|
| PATENT NO. | : 8,145,430 B2 |
| APPLICATION NO. | : 11/373684 |
| DATED | : March 27, 2012 |
| INVENTOR(S) | : Richard A. Friesner et al. |

It is certified that error appears in the above-identified patent and that said Letters Patent is hereby corrected as shown below:

On the Title Page

Item (56) References Cited, OTHER PUBLICATIONS, Col. 2, line 1, delete "J.." and insert -- J. --.

Item (56) References Cited, OTHER PUBLICATIONS, Col. 2, line 22, delete "AffinityAffinityof" and insert -- Affinity of --.

Item (57) Abstract, Col. 2, line 13, delete "salvation" and insert -- solvation --.

In the Claims

Col. 31, line 4, claim 17, after "1" insert -- in --.

Col. 32, line 18, claim 23, delete "interactions" and insert -- interaction --.

Col. 32, line 45, claim 23, delete "score.);" and insert -- score); --.

Col. 32, line 58, claim 23, after "charge" insert -- . --.

Col. 32, line 65, claim 24, delete "22" and insert -- 23 --.

Col. 32, line 66, claim 24, delete "22" and insert -- 23 --.

Col. 33, line 20, claim 26, after "is" insert -- further --.

Col. 33, line 26, claim 26, delete "claim 31" and insert -- claim 20 --.

Col. 33, line 38, claim 27, delete "interactions" and insert -- interaction --.

Col. 33, line 60, claim 28, delete "interactions" and insert -- interaction --.

Signed and Sealed this
Twenty-fourth Day of February, 2015

Michelle K. Lee
*Deputy Director of the United States Patent and Trademark Office*

CERTIFICATE OF CORRECTION (continued)
U.S. Pat. No. 8,145,430 B2

Col. 34, line 15, claim 29, delete "interactions" and insert -- interaction --.

Col. 34, line 57, claim 34, delete "interactions" and insert -- interaction --.

Col. 36, line 3, claim 38, delete "interactions" and insert -- interaction --.

Col. 36, line 26, claim 40, after "1" delete "or".